US008956833B2

(12) United States Patent
Swartz

(10) Patent No.: US 8,956,833 B2
(45) Date of Patent: Feb. 17, 2015

(54) METHODS FOR CONTROL OF FLUX IN METABOLIC PATHWAYS THROUGH ENZYME RELOCATION

(75) Inventor: James R. Swartz, Menlo Park, CA (US)

(73) Assignees: GreenLight Biosciences, Inc., Medford, MA (US); The Board of Trustees of the Leland Stanford Junior University, Palo Alto, CA (US)

( * ) Notice: Subject to any disclaimer, the term of this patent is extended or adjusted under 35 U.S.C. 154(b) by 503 days.

(21) Appl. No.: 13/102,967

(22) Filed: May 6, 2011

(65) Prior Publication Data

US 2011/0275116 A1 Nov. 10, 2011

Related U.S. Application Data

(60) Provisional application No. 61/332,624, filed on May 7, 2010.

(51) Int. Cl.
| | |
|---|---|
| *C12N 1/21* | (2006.01) |
| *C12P 7/16* | (2006.01) |
| *C12N 15/63* | (2006.01) |
| *C12N 9/00* | (2006.01) |
| *C12P 7/42* | (2006.01) |
| *C12N 9/10* | (2006.01) |
| *C12N 9/88* | (2006.01) |
| *C12N 15/62* | (2006.01) |
| *C12P 7/62* | (2006.01) |
| *C12P 21/00* | (2006.01) |
| *C12P 23/00* | (2006.01) |
| *C12N 1/06* | (2006.01) |
| *C12P 13/00* | (2006.01) |
| *C12P 7/00* | (2006.01) |
| *C12P 5/00* | (2006.01) |

(52) U.S. Cl.
CPC .............. *C12P 7/42* (2013.01); *C07K 2319/034* (2013.01); *C12N 9/1029* (2013.01); *C12N 9/88* (2013.01); *C12N 15/625* (2013.01); *C12P 7/16* (2013.01); *C12P 7/625* (2013.01); *C12P 23/00* (2013.01); *Y02E 50/10* (2013.01)
USPC ......... 435/69.8; 435/41; 435/252.3; 435/183; 435/132; 435/160; 435/166

(58) Field of Classification Search
None
See application file for complete search history.

(56) References Cited

U.S. PATENT DOCUMENTS

| | | | |
|---|---|---|---|
| 3,684,652 | A | 8/1972 | Nakayama et al. |
| 3,950,357 | A | 4/1976 | Kahan et al. |
| RE28,886 | E | 6/1976 | Nakayama et al. |
| 4,006,060 | A | 2/1977 | Kahan et al. |
| 4,194,047 | A | 3/1980 | Christensen et al. |
| 4,270,537 | A | 6/1981 | Romaine |
| 4,292,436 | A | 9/1981 | Liu et al. |
| 4,329,481 | A | 5/1982 | Liu et al. |
| 4,374,772 | A | 2/1983 | Hazen et al. |
| 4,438,201 | A | 3/1984 | Kubo et al. |
| 4,458,066 | A | 7/1984 | Caruthers et al. |
| 4,460,689 | A | 7/1984 | Foor et al. |
| 4,596,556 | A | 6/1986 | Morrow et al. |
| 4,790,824 | A | 12/1988 | Morrow et al. |
| 4,886,499 | A | 12/1989 | Cirelli et al. |
| 4,940,460 | A | 7/1990 | Casey et al. |
| 4,941,880 | A | 7/1990 | Burns |
| 4,946,783 | A | 8/1990 | Beckwith et al. |
| 4,950,603 | A | 8/1990 | Ingolia et al. |
| 5,001,055 | A | 3/1991 | Imahori et al. |
| 5,015,235 | A | 5/1991 | Crossman |
| 5,064,413 | A | 11/1991 | McKinnon et al. |
| 5,070,020 | A | 12/1991 | Ingolia et al. |
| 5,141,496 | A | 8/1992 | Dalto et al. |
| 5,190,521 | A | 3/1993 | Hubbard et al. |
| 5,312,335 | A | 5/1994 | McKinnon et al. |
| 5,319,122 | A | 6/1994 | Friedman |
| 5,328,483 | A | 7/1994 | Jacoby |
| 5,334,144 | A | 8/1994 | Alchas et al. |
| 5,339,163 | A | 8/1994 | Homma et al. |
| 5,383,851 | A | 1/1995 | McKinnon, Jr. et al. |
| 5,417,662 | A | 5/1995 | Hjertman et al. |
| 5,436,131 | A | 7/1995 | Condra et al. |
| 5,466,220 | A | 11/1995 | Brenneman |
| 5,480,381 | A | 1/1996 | Weston |
| 5,503,627 | A | 4/1996 | McKinnon et al. |

(Continued)

FOREIGN PATENT DOCUMENTS

| | | |
|---|---|---|
| EP | 0377295 A1 | 7/1990 |
| EP | 0444775 A1 | 9/1991 |

(Continued)

OTHER PUBLICATIONS

Danese, P.D. and Silhavy, T.J. "Targeting and Assembly of Periplasmic and Outer-Membrane Proteins in *Escherichia coli*" Annu. Rev. Genet. 1998, 32, pp. 59-94.*
Ward et al., Genomic insights into methanotrophy: the complete genome sequence of *Methylococcus capsulatus* (Bath). PLOS Biology. 2004;2(10):1616-28.
Collins-Racie et al., Production of recombinant bovine enterokinase catalytic subunit in *Escherichia coli* using the novel secretory fusion partner DsbA. Biotechnology (NY). Sep. 1995;13(9):982-7.
[No Author Listed] Biolistic® Particle Delivery System Bibliography. Bio-Rad Technical Bulletin #1687. Bio-Rad Laboratories. Aug. 2004, 12 pages.

(Continued)

*Primary Examiner* — Jon P Weber
*Assistant Examiner* — Aaron J Kosar
(74) *Attorney, Agent, or Firm* — Wolf, Greenfield & Sacks, P.C.; C. Hunter Baker; Heather J. DiPietrantonio

(57) ABSTRACT

Genetically manipulated cells, lysates of such cells, systems, and methods of use thereof are provided, where one or more enzymes in a pathway of interest are genetically modified to incorporate a peptide sequence that provides for relocation of the protein, e.g., to the periplasm, so as to sequester the enzyme, and where the enzyme controls flux in the pathway of interest.

38 Claims, 5 Drawing Sheets

(56) References Cited

U.S. PATENT DOCUMENTS

| | | | |
|---|---|---|---|
| 5,520,639 A | 5/1996 | Peterson et al. |
| 5,527,288 A | 6/1996 | Gross et al. |
| 5,569,189 A | 10/1996 | Parsons |
| 5,593,856 A | 1/1997 | Choi et al. |
| 5,599,302 A | 2/1997 | Lilley et al. |
| 5,649,912 A | 7/1997 | Peterson |
| 5,672,497 A | 9/1997 | Cox et al. |
| 5,704,911 A | 1/1998 | Parsons |
| 5,871,922 A | 2/1999 | Salmond et al. |
| 5,893,397 A | 4/1999 | Peterson et al. |
| 5,993,412 A | 11/1999 | Deily et al. |
| 6,168,931 B1 | 1/2001 | Swartz et al. |
| 6,387,667 B1 | 5/2002 | Maruyama et al. |
| 6,440,688 B1 | 8/2002 | Bruce et al. |
| 6,472,169 B1 | 10/2002 | Frost et al. |
| 6,531,299 B1 | 3/2003 | Khosla et al. |
| 6,746,859 B1 | 6/2004 | LaVallie |
| 6,921,659 B2 | 7/2005 | Joly |
| 6,994,986 B2 | 2/2006 | Swartz et al. |
| 7,041,479 B2 | 5/2006 | Swartz et al. |
| 7,223,390 B2 | 5/2007 | Brown |
| 7,226,767 B2 | 6/2007 | Maruyama et al. |
| 7,312,049 B2 | 12/2007 | Calhoun et al. |
| 7,338,789 B2 | 3/2008 | Swartz et al. |
| 7,341,852 B2 | 3/2008 | Voloshin et al. |
| 7,351,563 B2 | 4/2008 | Swartz et al. |
| 2002/0058303 A1 | 5/2002 | Swartz et al. |
| 2002/0127633 A1 | 9/2002 | Dilley et al. |
| 2003/0022178 A1 | 1/2003 | Schneewind et al. |
| 2003/0113778 A1 | 6/2003 | Schulte et al. |
| 2004/0002103 A1 | 1/2004 | Short |
| 2004/0038250 A1 | 2/2004 | Nunez et al. |
| 2004/0209321 A1 | 10/2004 | Swartz et al. |
| 2005/0054044 A1 | 3/2005 | Swartz et al. |
| 2006/0281148 A1 | 12/2006 | Swartz et al. |
| 2007/0111283 A1 | 5/2007 | Cannon et al. |
| 2007/0154983 A1 | 7/2007 | Calhoun et al. |
| 2007/0202198 A1 | 8/2007 | Purcell |
| 2008/0131925 A1 | 6/2008 | Berk et al. |
| 2009/0124012 A1 | 5/2009 | Nikolsky et al. |
| 2009/0275096 A1 | 11/2009 | Burgard et al. |
| 2009/0312539 A1 | 12/2009 | Gnanaprakasam et al. |
| 2010/0291653 A1 | 11/2010 | Ness et al. |
| 2011/0008867 A1 | 1/2011 | Zarur et al. |
| 2011/0099670 A1 | 4/2011 | Koops et al. |
| 2011/0269198 A1 | 11/2011 | Klein-Marcuschamer |
| 2012/0052547 A1 | 3/2012 | Swartz |
| 2012/0070870 A1 | 3/2012 | Way et al. |
| 2013/0065878 A1 | 3/2013 | Blake et al. |

FOREIGN PATENT DOCUMENTS

| | | | |
|---|---|---|---|
| EP | 0553821 A1 | 8/1993 |
| EP | 1 433 856 A1 | 6/2004 |
| EP | 1502956 A1 | 2/2005 |
| EP | 1939210 A1 | 7/2008 |
| EP | 2204453 A1 | 7/2010 |
| GB | 2 018 822 A | 10/1979 |
| WO | WO 97/13537 A1 | 4/1997 |
| WO | WO 97/37705 A1 | 10/1997 |
| WO | WO 98/07690 A1 | 2/1998 |
| WO | WO 99/34850 A1 | 7/1999 |
| WO | 00/03581 A1 | 1/2000 |
| WO | WO 00/55353 A1 | 9/2000 |
| WO | WO 2005/098048 A1 | 10/2005 |
| WO | WO 2007/053655 A2 | 5/2007 |
| WO | WO 2007/137144 A2 | 11/2007 |
| WO | WO 2008/002661 A2 | 1/2008 |
| WO | WO 2008/002663 A2 | 1/2008 |
| WO | WO 2008/002673 A2 | 1/2008 |
| WO | WO 2008/066583 A2 | 6/2008 |
| WO | WO 2008/088884 A2 | 7/2008 |
| WO | WO 2008/094546 A2 | 8/2008 |
| WO | WO 2010/046713 A2 | 4/2010 |
| WO | WO 2010/074760 A1 | 7/2010 |
| WO | WO 2010/077806 A1 | 7/2010 |
| WO | 2011/017560 A1 | 2/2011 |
| WO | WO 2011/072287 A2 | 6/2011 |
| WO | 2011/140516 A2 | 11/2011 |
| WO | 2012/030980 A1 | 3/2012 |

OTHER PUBLICATIONS

[No Author Listed] Biapenem. Drugs Fut. 1994;19(7):631-637.
Adams et al., Hindered dialkylamino nucleoside phosphite reagents in the synthesis of two DNA 51-mers. J Am Chem Soc. 1983;105(3):661-3.
Alber et al., Malonyl-coenzyme A reductase in the modified 3-hydroxypropionate cycle for autotrophic carbon fixation in archaeal *Metallosphaera* and *Sulfolobus* spp. J Bacteriol. Dec. 2006;188(24):8551-9. Epub Oct. 13, 2006.
Allain, Cell-free ethanol production: the future of fuel ethanol? J Chem Technol Biotechnol. 2007;82:117-20.
Alper et al., Tuning genetic control through promoter engineering. Proc Natl Acad Sci U S A. Sep. 6, 2005;102(36):12678-83. Epub Aug. 25, 2005.
Alves-Pereira et al., CDP-alcohol hydrolase, a very efficient activity of the 5'-nucleotidase/udp-sugar hydrolase encoded by the usha gene of *Yersinia intermedia* and *Escherichia coli*. J Bacteriol. Sep. 15, 2008;190(18):6153-61. Published ahead of print Jul. 18, 2008 , doi:10.1128/JB.00658-08.
Anthony et al., Optimization of the mevalonate-based isoprenoid biosynthetic pathway in *Escherichia coli* for production of the antimalarial drug precursor amorpha-4,11-diene. Metab Eng. Jan. 2009;11(1):13-9. Epub Aug. 12, 2008.
Atsumi et al., Metabolic engineering of *Escherichia coli* for 1-butanol production. Metab Eng. Nov. 2008;10(6):305-11. Epub Sep. 14, 2007.
Atsumi et al., Non-fermentative pathways for synthesis of branched-chain higher alcohols as biofuels. Nature. Jan. 3, 2008;451(7174):86-9.
Bateson et al., Olivanic acid analogues. Part 6. Biomimetic synthesis of (±)-PS-5, (±)-6-Epi-PS-5, and (±)-benzyl MM22381. J Chem Soc Perkin Trans 1. 1990;1793-1801.
Baum et al., beta-Galactosidase containing a human immunodeficiency virus protease cleavage site is cleaved and inactivated by human immunodeficiency virus protease. Proc Natl Acad Sci U S A. Dec. 1990;87(24):10023-7.
Beaucage et al., Deoxynucleoside phosphoramidites—A new class of key intermediates for deoxypolynucleotide synthesis. Tetra Lett. 1981;22(20):1859-62.
Belousov et al., Sequence-specific targeting and covalent modification of human genomic DNA. Nucleic Acids Res. Sep. 1, 1997;25(17):3440-4.
Benton et al., Screening lambdagt recombinant clones by hybridization to single plaques in situ. Science. Apr. 8, 1977;196(4286):180-2.
Berge et al., Pharmaceutical salts. J Pharmaceut Sci. Jan. 1977;66(1):1-19.
Blommers et al., Effects of the introduction of L-nucleotides into DNA. Solution structure of the heterochiral duplex d(G-C-G-(L)T-G-C-G).d(C-G-C-A-C-G-C) studied by NMR spectroscopy. Biochemistry. Jun. 28, 1994;33(25):7886-96.
Bodner et al., Non-heme iron oxygenases generate natural structural diversity in carbapenem antibiotics. J Am Chem Soc. Jan. 13, 2010;132(1):12-3.
Boiteux et al., Design of glycolysis. Philos Trans R Soc Lond B Biol Sci. Jun. 26, 1981;293(1063):5-22.
Bongaerts et al., Metabolic engineering for microbial production of aromatic amino acids and derived compounds. Metab Eng. Oct. 2001;3(4):289-300.
Boyer et al., Cell-free synthesis and maturation of [FeFe] hydrogenases. Biotechnol Bioeng. Jan. 1, 2008;99(1):59-67.
Bradley, Star role for bacteria in controlling flu pandemic? Nat Rev Drug Discov. Dec. 2005;4(12):945-6.
Brown et al., Chemical synthesis and cloning of a tyrosine tRNA gene. Methods Enzymol. 1979;68:109-51.

(56) References Cited

OTHER PUBLICATIONS

Buist et al., Different subcellular locations of secretome components of Gram-positive bacteria. Microbiology. Oct. 2006;152(Pt 10):2867-74.

Calhoun et al., An economical method for cell-free protein synthesis using glucose and nucleoside monophosphates. Biotechnol Prog. Jul.-Aug. 2005;21(4):1146-53.

Calhoun et al., Energizing cell-free protein synthesis with glucose metabolism. Biotechnol Bioeng. Jun. 5, 2005;90(5):606-13.

Calhoun et al., Energy systems for ATP regeneration in cell-free protein synthesis reactions. Methods in Molecular Biology. In vitro transcription and translation protocols. 2007, 375(2), 3-17.

Calhoun et al., Total amino acid stabilization during cell-free protein synthesis reactions. J Biotechnol. May 17, 2006;123(2):193-203. Epub Jan. 26, 2006.

Campbell et al., The CTP:phosphocholine cytidylyltransferase encoded by the licC gene of Streptococcus pneumoniae: cloning, expression, purification, and characterization. Biochim Biophys Acta. Dec. 30, 2001;1534(2-3):85-95.

Chandran et al., Phosphoenolpyruvate availability and the biosynthesis of shikimic acid. Biotechnol Prog. May-Jun. 2003;19(3):808-14.

Chang et al., YPA: an integrated repository of promoter features in Saccharomyces cerevisiae. Nucleic Acids Res. Jan. 2011;39(Database issue):D647-52. Epub Nov. 2, 2010.

Chen et al., A modified osmotic shock for periplasmic release of a recombinant creatinase from Escherichia coli. Biochem Eng J. 2004;19:211-5.

Chen et al., Crystal structures of penicillin-binding protein 6 from Escherichia coli. J Am Chem Soc. Oct. 14, 2009;131(40):14345-54.

Chen et al., High-level accumulation of a recombinant antibody fragment in the periplasm of Escherichia coli requires a triple-mutant (degP prc spr) host strain. Biotechnol Bioeng. Mar. 5, 2004;85(5):463-74.

Chiu et al., Site-directed, Ligase-Independent Mutagenesis (SLIM): a single-tube methodology approaching 100% efficiency in 4 h. Nucleic Acids Res. Dec. 7, 2004;32(21):e174.

Chong et al., Single-column purification of free recombinant proteins using a self-cleavable affinity tag derived from a protein splicing element. Gene. Jun. 19, 1997;192(2):271-81.

Choubey et al., Molecular characterization and localization of Plasmodium falciparum choline kinase. Biochim Biophys Acta. Jul. 2006;1760(7):1027-38.

Coulthurst et al., Regulation and biosynthesis of carbapenem antibiotics in bacteria. Nat Rev Microbiol. Apr. 2005;3(4):295-306. Erratum included.

Dahiyat et al., De novo protein design: fully automated sequence selection. Science. Oct. 3, 1997;278(5335):82-7.

Dahl et al., Isolation and characterization of Chinese hamster ovary cells defective in the intracellular metabolism of low density lipoprotein-derived cholesterol. J Biol Chem. Mar. 5, 1992;267(7):4889-96.

Dani et al., Isolation and characterization of a thylakoid membrane module showing partial light and dark reactions. Biochim Biophys Acta. May 15, 2005;1669(1):43-52.

Daniell et al., Transformation of the cyanobacterium Anacystis nidulans 6301 with the Escherichia coli plasmid pBR322. Proc Natl Acad Sci U S A. Apr. 1986;83(8):2546-50.

Datsenko et al., One-step inactivation of chromosomal genes in Escherichia coli K-12 using PCR products. Proc Natl Acad Sci U S A. Jun. 6, 2000;97(12):6640-5.

De Boer et al., Protein targeting towards the thylakoid lumen of chloroplasts: proper localization of fusion proteins is only observed in vivo. EMBO J. Oct. 1991;10(10):2765-72.

De Mey et al., Construction and model-based analysis of a promoter library for E. coli: an indispensable tool for metabolic engineering. BMC Biotechnol. Jun. 18, 2007;7:34.

Dietrich et al., A novel semi-biosynthetic route for artemisinin production using engineered substrate-promiscuous P450(BM3). ACS Chem Biol. Apr. 17, 2009;4(4):261-7.

Dingwall et al., The nucleoplasmin nuclear location sequence is larger and more complex than that of SV-40 large T antigen. J Cell Biol. Sep. 1988;107(3):841-9.

Draper et al., Ti plasmid homologous sequences present in tissues from agrobacterium plasmid-transformed petunia protoplasts. Plant Cell Physiol. 1982;23(3):451-8.

Elander, Industrial production of beta-lactam antibiotics. Appl Microbiol Biotechnol. Jun. 2003;61(5-6):385-92. Epub Apr. 3, 2003.

Erb et al., Carboxylation mechanism and stereochemistry of crotonyl-CoA carboxylase/reductase, a carboxylating enoyl-thioester reductase. Proc Natl Acad Sci U S A. Jun. 2, 2009;106(22):8871-6. Epub May 20, 2009.

Erb et al., Synthesis of C5-dicarboxylic acids from C2-units involving crotonyl-CoA carboxylase/reductase: The ethylmalonyl-CoA pathway. Proc Nat Acad Sci. Jun. 4, 2007;104(25):10631-6.

Evans et al., The asymmetric synthesis of β-lactam antibiotics—IV. A formal synthesis of thienamycin. Tetra Lett. 1986;27(41):4961-4.

Flores et al., Pathway engineering for the production of aromatic compounds in Escherichia coli. Nat Biotechnol. May 1996;14(5):620-3.

Freeman et al., Four enzymes define the incorporation of coenzyme A in thienamycin biosynthesis. Proc Natl Acad Sci U S A. Aug. 12, 2008;105(32):11128-33. Epub Aug. 4, 2008.

Freeman et al., A comparison of methods for plasmid delivery into plant protoplasts. Plant Cell Physiol. 1984;25(8):1353-65.

Frenkel et al., 7,12-dimethylbenz[a]anthracene induces oxidative DNA modification in vivo. Free Radic Biol Med. Sep. 1995;19(3):373-80.

Friesen et al., Purification and Kinetic Characterization of CTP: Phosphocholine Cytidylyltransferase from Saccharomyces cerevisiae. Protein Expression and Purification. Feb. 2001;21(1):141-8.

Fromm et al., Stable transformation of maize after gene transfer by electroporation. Nature. Feb. 27-Mar. 5, 1986;319(6056):791-3.

Fujio et al., Construction of a plasmid carrying both CTP synthetase and a fused gene formed from cholinephosphate cytidylyltransferase and choline kinase genes and its application to industrial CDP-choline production: enzymatic production of CDP-choline from orotic acid (Part II). Biosci Biotechnol Biochem. Jun. 1997;61(6):960-4.

Gaspar et al., High yields of 2,3-butanediol and mannitol in Lactococcus lactis through engineering of NAD$^+$ cofactor recycling. Appl Environ Microbiol. Oct. 2011;77(19):6826-35. Epub Aug. 12, 2011. Supplemental material included.

Ger et al., A single Ser-180 mutation desensitizes feedback inhibition of the phenylalanine-sensitive3-deoxy-D-arabino-heptulosonate 7-phosphate (DAHP) synthetase in Escherichia coli. J Biochem. Nov. 1994;116(5):986-90.

Gibellini et al., Biochemical characterization of the initial steps of the Kennedy pathway in Trypanosoma brucei: the ethanolamine and choline kinases. Biochem J. 2008;415:135-44. Supplemental data attached.

Goerke et al., Development of cell-free protein synthesis platforms for disulfide bonded proteins. Biotechnol Bioeng. Feb. 1, 2008;99(2):351-67. Epub Jul. 11, 2007.

Gordon-Kamm et al., Transformation of Maize Cells and Regeneration of Fertile Transgenic Plants. Plant Cell. Jul. 1990;2(7):603-618.

Gosset et al., A direct comparison of approaches for increasing carbon flow to aromatic biosynthesis in Escherichia coli. J Ind Microbiol. Jul. 1996;17(1):47-52.

Grabowski, Enantiopure drug synthesis: from methyldopa to imipenem to efavirenz. Chirality. 2005;17 Suppl:S249-59.

Grieco et al., .beta.-Lactam antibiotics: a formal stereocontrolled total synthesis of (.+-.)-thienamycin. J Am Chem Soc. 1984;106(21):6414-7.

Grunstein et al., Colony hybridization: a method for the isolation of cloned DNAs that contain a specific gene. Proc Natl Acad Sci U S A. Oct. 1975;72(10):3961-5.

Hamed et al., Carboxymethylproline synthase catalysed syntheses of functionalized N-heterocycles. Chem Commun (Camb). Mar. 7, 2010;46(9):1413-5. Epub Jan. 12, 2010.

(56) References Cited

OTHER PUBLICATIONS

Hamed et al., Evidence that thienamycin biosynthesis proceeds via C-5 epimerization: I catalyzes the formation of (2S,5S)-trans-carboxymethylproline. Chembiochem. Jan. 26, 2009;10(2):246-50.
Hawley et al., Compilation and analysis of *Escherichia coli* promoter DNA sequences. Nucleic Acids Res. Apr. 25, 1983;11(8):2237-55.
Herrmann, The shikimate pathway as an entry to aromatic secondary metabolism. Plant Physiol. Jan. 1995;107(1):7-12.
Hikita et al., Effects of total hydrophobicity and length of the hydrophobic domain of a signal peptide on in vitro translocation efficiency. J Biol Chem. 1992;267:4882-8.
Hikita et al., The requirement of a positive charge at the amino terminus can be compensated for by a longer central hydrophobic stretch in the functioning of signal peptides. J Biol Chem. 1992;267:12375-9.
Hodgson et al., π-Allyltricarbonyliron lactone complexes in synthesis: application to the synthesis of the β-lactam antibiotic (+)-thienamycin. J Chem Soc Chem Comm. 1984;8:494-6.
Inouye, The discovery of mRNA interferases: implication in bacterial physiology and application to biotechnology. J Cell Physiol. Dec. 2006;209(3):670-6.
Ishii et al., DBTBS: a database of *Bacillus subtilis* promoters and transcription factors. Nucleic Acids Res. Jan. 1, 2001;29(1):278-80.
Jacobi et al., Formal Total Syntheses of the β-Lactam Antibiotics Thienamycin and PS-5. J Org Chem. 1996;61(7):2413-27.
Jang et al., Sugar sensing in higher plants. Plant Cell. Nov. 1994;6(11):1665-79.
Jermutus et al., Recent advances in producing and selecting functional proteins by using cell-free translation. Curr Opin Biotechnol. Oct. 1998;9(5):534-48.
Jewett et al., An integrated cell-free metabolic platform for protein production and synthetic biology. Mol Syst Biol. 2008;4:220. Epub Oct. 14, 2008.
Jewett et al., Mimicking the *Escherichia coli* cytoplasmic environment activates long-lived and efficient cell-free protein synthesis. Biotechnol Bioeng. Apr. 5, 2004;86(1):19-26.
Kahan et al., Thienamycin, a new beta-lactam antibiotic. I. Discovery, taxonomy, isolation and physical properties. J Antibiot (Tokyo). Jan. 1979;32(1):1-12.
Kahan et al., Thienamycin: development of imipenen-cilastatin. J Antimicrob Chemother. Dec. 1983;12 Suppl D:1-35.
Kalderon et al., A short amino acid sequence able to specify nuclear location. Cell. Dec. 1984;39(3 Pt 2):499-509.
Kametani et al., Studies on the syntheses of heterocyclic compounds. 800. A formal total synthesis of (.+-.)-thienamycin and a (.+-.)-decysteaminylthienamycin derivative. J Am Chem Soc. 1980;102(6):2060-5.
Kapust et al., Tobacco etch virus protease: mechanism of autolysis and rational design of stable mutants with wild-type catalytic proficiency. Protein Eng. Dec. 2001;14(12):993-1000.
Kikuchi et al., Mutational analysis of the feedback sites of phenylalanine-sensitive 3-deoxy-D-arabino-heptulosonate-7-phosphate synthase of *Escherichia coli*. Appl Environ Microbiol. Feb. 1997;63(2):761-2.
Kim et al., Expression, purification, and characterization of choline kinase, product of the cki gene from *Saccharomyces cerevisiae*. J Bio Chem. 1998;273(12):6844-6852.
Kim et al., Prolonged cell-free protein synthesis using dual energy sources: Combined use of creatine phosphate and glucose for the efficient supply of ATP and retarded accumulation of phosphate. Biotechnol Bioeng. Aug. 15, 2007;97(6):1510-5.
Kimmel, Identification and characterization of specific clones: strategy for confirming the validity of presumptive clones. Methods Enzymol. 1987;152:507-11.
Kindle, High-frequency nuclear transformation of *Chlamydomonas reinhardtii*. Proc Natl Acad Sci U S A. Feb. 1990;87(3):1228-32.
Knapp et al., Cell-free production of active *E. coli* thioredoxin reductase and glutathione reductase. FEBS Lett. Feb. 13, 2004;559(1-3):66-70.

Knop et al., Hydroaromatic equilibration during biosynthesis of shikimic acid. J Am Chem Soc. Oct. 24, 2001;123(42):10173-82.
Ko et al., Targeting of proteins to the thylakoid lumen by the bipartite transit peptide of the 33 kd oxygen-evolving protein. EMBO J. Nov. 1989;8(11):3187-94.
Krämer et al., Metabolic engineering for microbial production of shikimic acid. Metab Eng. Oct. 2003;5(4):277-83.
Kumagai et al., Current status of oral carbapenem development. Curr Med Chem—Anti-Infective Agents. Jan. 2002;1(1):1-14.
Kunkel, Rapid and efficient site-specific mutagenesis without phenotypic selection. Proc Natl Acad Sci U S A. Jan. 1985;82(2):488-92.
Lee et al., Fermentative production of thymidine by a metabolically engineered *Escherichia coli* strain. Appl Environ Microbiol. Apr. 2009;75(8):2423-32. Epub Feb. 27, 2009.
Lee et al., Systems metabolic engineering of *Escherichia coli* for L-threonine production. Mol Syst Biol. 2007;3:149. Epub Dec. 4, 2007.
Lee, High cell-density culture of *Escherichia coli*. Trends Biotechnol. Mar. 1996;14(3):98-105.
Liu et al., Streamlining *Escherichia coli* S30 extract preparation for economical cell-free protein synthesis. Biotechnol Prog. Mar.-Apr. 2005;21(2):460-5.
Ludwig et al., Mutations affecting export and activity of cytolysin A from *Escherichia coli*. J Bacteriol. Aug. 2010;192(15):4001-11. Epub May 28, 2010.
Mackle et al., Role of signal peptides in targeting of proteins in cyanobacteria. J Bacteriol. Apr. 1994;176(7):1857-64.
Mandel et al., Modular synthesis of pantetheine and phosphopantetheine. Org Lett. Dec. 23, 2004;6(26):4801-3.
Martin et al., Engineering a mevalonate pathway in *Escherichia coli* for production of terpenoids. Nat Biotechnol. Jul. 2003;21(7):796-802. Epub Jun. 1, 2003.
Mergulhão et al., Analysis of factors affecting the periplasmic production of recombinant proteins in *Escherichia coli*. J Microbiol Biotechnol. Aug. 2007;17(8):1236-41.
Mergulhão et al., Recombinant protein secretion in *Escherichia coli*. Biotechnol Adv. May 2005;23(3):177-202. Epub Jan. 8, 2005.
Meyerhof, New investigations in the kinetics of cell free alcoholic fermentation. Antonie Van Leeuwenhoek. Jan.-Apr. 1947;12(1-4):140-4.
Michel-Reydellet et al., Amino acid stabilization for cell-free protein synthesis by modification of the *Escherichia coli* genome. Metab Eng. Jul. 2004;6(3):197-203.
Muchmore et al., Crystal structure of glutamine phosphoribosylpyrophosphate amidotransferase from *Escherichia coli*.Protein Sci. Jan. 1998;7(1):39-51.
Muktiono et al., Isolation and purification assay of ex vivo photosystem II D1 protein toward integrated biointeraction analysis. Anal Bioanal Chem. Feb. 2008;390(4):1195-202. Epub Jan. 3, 2008.
Murphy, Use of bacteriophage lambda recombination functions to promote gene replacement in *Escherichia coli*. J Bacteriol. Apr. 1998;180(8):2063-71.
Myers et al., Determination of imipenem and cilastatin in serum by high-pressure liquid chromatography. Antimicrob Agents Chemother. Jul. 1984;26(1):78-81.
Narang et al., Improved phosphotriester method for the synthesis of gene fragments. Methods Enzymol. 1979;68:90-8.
Neidhardt et al., Culture medium for enterobacteria. J Bacteriol. Sep. 1974;119(3):736-47.
Nunez et al., The Biosynthetic Gene Cluster for the β-Lactam Carbapenem Thienamycin in *Streptomyces cattleya*. Chem Biol. Apr. 2003;10(4):301-11.
Ono et al., Photosynthetic electron transport and phosphorylation reactions in thylakoid membranes from the blue-green alga *Anacystis nidulans*. Biochim Biophys Acta. Jun. 8, 1978;502(3):477-85.
Park et al., Metal-catalyzed oxidation of phenylalanine-sensitive 3-deoxy-D-arabino heptulosonate-7-phosphate synthase from *Escherichia coli*: inactivation and destabilization by oxidation of active-site cysteines. J Bacteriol. Mar. 1999;181(5):1636-42.
Patnaik et al., Engineering of *Escherichia coli* central metabolism for aromatic metabolite production with near theoretical yield. Appl Environ Microbiol. Nov. 1994;60(11):3903-8.

(56) References Cited

OTHER PUBLICATIONS

Pitera et al., Balancing a heterologous mevalonate pathway for improved isoprenoid production in *Escherichia coli*. Metab Eng. Mar. 2007;9(2):193-207. Epub Nov. 23, 2006.
Qi et al., A one-step PCR-based method for rapid and efficient site-directed fragment deletion, insertion, and substitution mutagenesis. J Virolog Meth. Apr. 2008;149(1):85-90.
Ray et al., Mutational analysis of the catalytic and feedback sites of the tryptophan-sensitive 3-deoxy-D-arabino-heptulosonate-7-phosphate synthase of *Escherichia coli*. J Bacteriol. Dec. 1988;170(12):5500-6.
Reider et al., Total synthesis of thienamycin: a new approach from aspartic acid. Tetra Lett. 1982;23(22):2293-6.
Reyes et al., Genomic library screens for genes involved in n-butanol tolerance in *Escherichia coli*. PloS One. Mar. 8, 2011;6(3):e17678.
Rodríguez et al., Identification of transcriptional activators for thienamycin and cephamycin C biosynthetic genes within the thienamycin gene cluster from *Streptomyces cattleya*. Mol Microbiol. Aug. 2008;69(3):633-45.
Rodríguez et al., Transcriptional organization of ThnI-regulated thienamycin biosynthetic genes in *Streptomyces cattleya*. J Antibiot (Tokyo). Mar. 2010;63(3):135-8. Epub Jan. 22, 2010.
Sagui et al., Enzymatic synthesis of ω-carboxy-β-hydroxy-(1)-α-amino acids. Tetrahedron. May 26, 2008;64(22):5079-84.
Salis et al., Automated design of synthetic ribosome binding sites to control protein expression. Nat Biotechnol. Oct. 2009;27(10):946-50. Epub Oct. 4, 2009.
Salzmann et al., A stereocontrolled synthesis of (+)-thienamycin. J Am Chem Soc. 1980;102(19);6161-3.
Salzmann et al., A stereocontrolled, enantiomerically specific total synthesis of thienamycin. Philos Trans R Soc Lond B Biol Sci. May 16, 1980;289(1036):191-5.
Sarath et al., Use of GFP as a reporter for the analysis of sequence-specific proteases. Curr Protoc Protein Sci. Feb. 2001;Chapter 21 Unit 9 Suppl. 26: 21.9.1-.10.
Sato et al., Poly[(R)-3-hydroxybutyrate] formation in *Escherichia coli* from glucose through an enoyl-CoA hydratase-mediated pathway. J Biosci Bioeng, Jan. 2007;103(1):38-44.
Schlehuber et al., Prediction and identification of a permissive epitope insertion site in the vesicular stomatitis virus glycoprotein. J Virol. May 2004;78(10):5079-87.
Schnell, Protein targeting to the thylakoid membrane. Annu Rev Plant Physiol Plant Mol Biol. Jun. 1998;49:97-126.
Scopes, Glycolysis in cell-free systems. New beer in an old bottle: Eduard Buchner and the growth of biochemical knowledge. Ed A. Cornish-Bowden. 1997;151-8.
Sheen, Metabolic repression of transcription in higher plants. Plant Cell. Oct. 1990;2(10):1027-38.
Shi et al., Molecular properties, functions, and potential applications of NAD kinases. Acta Biochim Biophys Sin (Shanghai). May 2009;41(5):352-61.
Shine et al., Determinant of cistron specificity in bacterial ribosomes. Nature. Mar. 6, 1975;254(5495):34-8.
Simmons et al., Translational level is a critical factor for the secretion of heterologous proteins in *Escherichia coli*. Nat Biotechnol. May 1996;14(5):629-34.
Sleeman et al., Carboxymethylproline synthase (CarB), an unusual carbon-carbon bond-forming enzyme of the crotonase superfamily involved in carbapenem biosynthesis. J Biol Chem. Feb. 20, 2004;279(8):6730-6. Epub Nov. 18, 2003.
Soares et al., Periplasmic expression of human growth hormone via plasmid vectors containing the lambdaPL promoter: use of HPLC for product quantification. Protein Eng. Dec. 2003;16(12):1131-8.
Sorci et al., Nicotinamide mononucleotide synthetase is the key enzyme for an alternative route of NAD biosynthesis in *Francisella tularensis*.Proc Natl Acad Sci U S A. Mar. 3, 2009;106(9):3083-8. Epub Feb. 9, 2009. Supporting information attached, (S1-S31).
Stadtman et al., Metal-catalyzed oxidation of proteins. Physiological consequences. J Biol Chem. Feb. 5, 1991;266(4):2005-8.

Stapon et al., Synthesis of (3S,5R)-carbapenam-3-carboxylic acid and its role in carbapenem biosynthesis and the stereoinversion problem. J Am Chem Soc. Dec. 24, 2003;125(51):15746-7.
Stephanopoulos et al., Exploiting biological complexity for strain improvement through systems biology. Nat Biotechnol. Oct. 2004;22(10):1261-7.
Suzuki et al., Single protein production (SPP) system in *Escherichia coli*. Nat Protoc. 2007;2(7):1802-10.
Suzuki et al., Single protein production in living cells facilitated by an mRNA interferase. Mol Cell. Apr. 15, 2005;18(2):253-61.
Swartz et al., Advances in *Escherichia coli* production of therapeutic proteins. Curr Opin Biotechnol. Apr. 2001;12(2):195-201.
Swartz, Developing cell-free biology for industrial applications. J Ind Microbiol Biotechnol. Jul. 2006;33(7):476-85. Epub May 9, 2006. Review.
Sybesma et al., Increased production of folate by metabolic engineering of *Lactococcus lactis*. Appl Environ Microbiol. Jun. 2003;69(6):3069-76.
Tjalsma et al., Proteomics of protein secretion by *Bacillus subtilis*: separating the "secrets" of the secretome. Microbiol Mol Biol Rev. Jun. 2004;68(2):207-33.
Tracewell et al., Directed enzyme evolution: climbing fitness peaks one amino acid at a time. Curr Opin Chem Biol. Feb. 2009;13(1):3-9. Epub Feb. 25, 2009.
Tyo et al., Analysis of polyhydroxybutyrate flux limitations by systematic genetic and metabolic perturbations. Metab Eng. May 2010;12(3):187-95. Epub Oct. 30, 2009.
Van Bloois et al., Export of functional *Streptomyces coelicolor* alditol oxidase to the periplasm or cell surface of *Escherichia coli* and its application in whole-cell biocatalysis. Appl Microbiol Biotechnol. Jun. 2009;83(4):679-87. Epub Feb. 18, 2009.
Van Hees et al., Determination of low molecular weight organic acids in soil solution by HPLC. Talanta. Jan. 5, 1999;48(1):173-9.
Voloshin et al., Efficient and scalable method for scaling up cell free protein synthesis in batch mode. Biotechnol Bioeng. Aug. 20, 2005;91(4):516-21.
Wahl et al., Molecular hybridization of immobilized nucleic acids: theoretical concepts and practical considerations. Methods Enzymol. 1987;152:399-407.
Weaver et al., Cloning of an aroF allele encoding a tyrosine-insensitive 3-deoxy-D-arabino-heptulosonate 7-phosphate synthase. J Bacteriol. Nov. 1990;172(11):6581-4.
Welch et al., Studies on cell-free metabolism: Ethanol production by a yeast glycolytic system reconstituted from purified enzymes. J Biotechnol. 1985;2:257-73.
Wiechert et al., A universal framework for 13C metabolic flux analysis. Metab Eng. Jul. 2001;3(3):265-83.
Wiechert, 13C metabolic flux analysis. Metab Eng. Jul. 2001;3(3):195-206.
Wilen et al., Tetrahedron report No. 38: Strategies in optical resolutions. Tetrahedron. 1977;33:2725-2736.
Williamson et al., Biosynthesis of the beta-lactam antibiotic, thienamycin, by *Streptomyces cattleya*. J Biol Chem. Apr. 25, 1985;260(8):4637-47.
Wilson et al., The shikimic acid pathway and polyketide biosynthesis. J Indust Microbiol Biotechnol. 1998;20:299-303.
Withers et al., Identification of isopentenol biosynthetic genes from *Bacillus subtilis* by a screening method based on isoprenoid precursor toxicity. Appl Environ Microbiol. Oct. 2007;73(19):6277-83. Epub Aug. 10, 2007.
Woodrow et al., A sequential expression system for high-throughput functional genomic analysis. Proteomics. Nov. 2007;7(21):3870-9.
Woodrow et al., Rapid expression of functional genomic libraries. J Proteome Res. Dec. 2006;5(12):3288-300.
Wylie et al., A single point mutation in ctp synthetase of *Chlamydia trachomatis* confers resistance to cyclopentenyl cytosine. J Biol Chem. 1996;271:15393-400.
Yamaguchi et al., MqsR, a crucial regulator for quorum sensing and biofilm formation, is a GCU-specific mRNA interferase in *Escherichia coli*. J Biol Chem. Oct. 16, 2009;284(42):28746-53. Epub Aug. 18, 2009.

(56) References Cited

OTHER PUBLICATIONS

Yamaguchi et al., mRNA interferases, sequence-specific endoribonucleases from the toxin-antitoxin systems. Prog Mol Biol Transl Sci. 2009;85:467-500.
Yang et al., Export of methyl parathion hydrolase to the periplasm by the twin-arginine translocation pathway in *Escherichia coli*. J Agric Food Chem. Oct. 14, 2009;57(19):8901-5.
Yang et al., Rapid expression of vaccine proteins for B-cell lymphoma in a cell-free system. Biotechnol Bioeng. Mar. 5, 2005;89(5):503-11.
Yeo et al., *Plasmodium falciparum* CTP:phosphocholine cytidylyltransferase expressed in *Escherichia coli*: purification, characterization and lipid regulation. Biochem J. 1997;324:903-10.
Zamboni et al., (13)C-based metabolic flux analysis. Nat Protoc. 2009;4(6):878-92. Epub May 21, 2009.
Zawada et al., Effects of growth rate on cell extract performance in cell-free protein synthesis. Biotechnol Bioeng. Jul. 5, 2006;94(4):618-24.
Zawada et al., Maintaining rapid growth in moderate-density *Escherichia coli* fermentations. Biotechnol Bioeng. Feb. 20, 2005;89(4):407-15.
Zhang et al., Characterization of ChpBK, an mRNA interferase from *Escherichia coli*. J Biol Chem. Jul. 15, 2005;280(28):26080-8. Epub May 18, 2005.
Zhang et al., Characterization of YafO, an *Escherichia coli* toxin. J Biol Chem. Sep. 18, 2009;284(38):25522-31. Epub Jul. 17, 2009.
Zhang et al., Efficient regeneration of transgenic plants from rice protoplasts and correctly regulated expression of the foreign gene in the plants. Theor Appl Genet. 1988;76(6):835-40.
Zhang et al., Insights into the mRNA cleavage mechanism by MazF, an mRNA interferase. J Biol Chem. Feb. 4, 2005;280(5):3143-50. Epub Nov. 10, 2004.
Invitation to Pay Additional Fees for PCT/US2012/054195, mailed Jan. 30, 2013, 10 pp.
International Search Report and Written Opinion for PCT/US2012/054195, mailed Apr. 12, 2013, 22 pp.
International Preliminary Report on Patentability for PCT/US2011/035639, mailed Nov. 22, 2012, 12 pp.
International Preliminary Report on Patentability for PCT/US2011/049997, mailed Mar. 14, 2013, 8 pp.
Extended European Search Report for EP 09836804.6, mailed Jun. 4, 2012, 3 pp.
Office Action, mailed Jul. 2, 2012, for U.S. Appl. No. 12/644,998 ,11 pp.
Office Action, mailed Dec. 4, 2012, for U.S. Appl. No. 12/644,998, 9 pp.
GENBANK Submission; NIH/NCBI, Accession No. AAB59985; Ling et al.; Nov. 24, 1994.
GENBANK Submission; NIH/NCBI, Accession No. AAC73225; Blattner et al.; Sep. 1, 2011.
GENBANK Submission; NIH/NCBI, Accession No. AAC73226; Blattner et al.; Sep. 1, 2011.
GENBANK Submission; NIH/NCBI, Accession No. AAC73296; Blattner et al.; Sep. 1, 2011.
GENBANK Submission; NIH/NCBI, Accession No. AAC73346; Blattner et al.; Sep. 1, 2011.
GENBANK Submission; NIH/NCBI, Accession No. AAC73347; Blattner et al.; Sep. 1, 2011.
GENBANK Submission; NIH/NCBI, Accession No. AAC73842; Blattner et al.; Sep. 1, 2011.
GENBANK Submission; NIH/NCBI, Accession No. AAC73957; Blattner et al.; Sep. 1, 2011.
GENBANK Submission; NIH/NCBI, Accession No. AAC74746; Blattner et al.; Sep. 1, 2011.
GENBANK Submission; NIH/NCBI, Accession No. AAC74849; Blattner et al.; Sep. 1, 2011.
GENBANK Submission; NIH/NCBI, Accession No. AAC74924; Blattner et al.; Sep. 1, 2011.
GENBANK Submission; NIH/NCBI, Accession No. AAC75447; Blattner et al.; Sep. 1, 2011.
GENBANK Submission; NIH/NCBI, Accession No. AAC75821; Blattner et al.; Sep. 1, 2011.
GENBANK Submission; NIH/NCBI, Accession No. AAC75962; Blattner et al.; Sep. 1, 2011.
GENBANK Submission; NIH/NCBI, Accession No. AAC75963; Blattner et al.; Sep. 1, 2011.
GENBANK Submission; NIH/NCBI, Accession No. AAC76849; Blattner et al.; Sep. 1, 2011.
GENBANK Submission; NIH/NCBI, Accession No. AAC76898; Blattner et al.; Sep. 1, 2011.
GENBANK Submission; NIH/NCBI, Accession No. AAC76901; Blattner et al.; Sep. 1, 2011.
GENBANK Submission; NIH/NCBI, Accession No. AAC76995; Blattner et al.; Sep. 1, 2011.
GENBANK Submission; NIH/NCBI, Accession No. AAD38229; McGowan et al.; Jul. 14, 1999.
GENBANK Submission; NIH/NCBI, Accession No. AAD38230; McGowan et al.; Jul. 14, 1999.
GENBANK Submission; NIH/NCBI, Accession No. AAD38231; McGowan et al.; Jul. 14, 1999.
GENBANK Submission; NIH/NCBI, Accession No. ABA79923; Copeland et al.; Nov. 21, 2011.
GENBANK Submission; NIH/NCBI, Accession No. ACJ71669; Erb et al.; Dec. 10, 2008.
GENBANK Submission; NIH/NCBI, Accession No. AEW99093; Ou et al.; Dec. 29, 2011.
GENBANK Submission; NIH/NCBI, Accession No. AEW99097; Ou et al.; Dec. 29, 2011.
GENBANK Submission; NIH/NCBI, Accession No. AEW99098; Ou et al.; Dec. 29, 2011.
GENBANK Submission; NIH/NCBI, Accession No. BAA22406; Mori et al.; Sep. 20, 1997.
GENBANK Submission; NIH/NCBI, Accession No. BAB67276; Kawarabayasi et al.; Aug. 17, 2011.
GENBANK Submission; NIH/NCBI, Accession No. CAD18973; Nunez et al.; Apr. 15, 2005.
GENBANK Submission; NIH/NCBI, Accession No. CAD18975; Nunez et al.; Apr. 15, 2005.
GENBANK Submission; NIH/NCBI, Accession No. CAD18981; Nunez et al.; Apr. 15, 2005.
GENBANK Submission; NIH/NCBI, Accession No. CAD18985; Nunez et al.; Apr. 15, 2005.
GENBANK Submission; NIH/NCBI, Accession No. CAD18990; Nunez et al.; Apr. 15, 2005.
UniProtKB/Swiss-Prot; Accession No. P28269; Yonaha et al.; Jul. 11, 2012.
Baba et al., Construction of *Escherichia coli* K-12 in-frame, single-gene knockout mutants: the Keio collection. Mol Syst Biol. 2006;2:2006.0008. Epub Feb. 21, 2006.
Bodner et al., Definition of the common and divergent steps in carbapenem β-lactam antibiotic biosynthesis. Chembiochem. Sep. 19, 2011;12(14):2159-65. doi: 10.1002/cbic.201100366. Epub Aug. 24, 2011.
Bujara et al., Optimization of a blueprint for in vitro glycolysis by metabolic real-time analysis. Nat Chem Biol. May 2011;7(5):271-7. doi: 10.1038/nchembio.541. Epub Mar. 20, 2011.
Fischer et al., Metabolic flux profiling of *Escherichia coli* mutants in central carbon metabolism using GC-MS. Eur J Biochem. Mar. 2003;270(5):880-91.
Flores et al., Analysis of carbon metabolism in *Escherichia coli* strains with an inactive phosphotransferase system by (13)C labeling and NMR spectroscopy. Metab Eng. Apr. 2002;4(2):124-37.
Flores et al., Growth-rate recovery of *Escherichia coli* cultures carrying a multicopy plasmid, by engineering of the pentose-phosphate pathway. Biotechnol Bioeng. Aug. 20, 2004;87(4):485-94.
Fox et al., Methane monooxygenase from *Methylosinus trichosporium* OB3b. Purification and properties of a three-component system with high specific activity from a type II methanotroph. J Biol Chem. Jun. 15, 1989;264(17):10023-33.
Fradejas et al., The control of shikimic acid synthesis by tyrosine and phenylalamine. Biochem Biophys Res Commun. Jul. 26, 1961;5:320-3.

\* cited by examiner

Western blot of H-tagged AroG (expressed from pET backbone)

METHODS FOR CONTROL OF FLUX IN METABOLIC PATHWAYS THROUGH ENZYME RELOCATION

RELATED APPLICATIONS

This application claims priority under 35 U.S.C. §119(e) to U.S. provisional application, U.S. Ser. No. 61/332,624, filed May 7, 2010, which is incorporated herein by reference.

BACKGROUND OF THE INVENTION

Production of chemicals via synthetic enzymatic pathways in microbial hosts has proven useful for many important classes of molecules, including isoprenoids, polyketides, nonribosomal peptides, bioplastics, and chemical building blocks. Due to the inherent modularity of biological information, synthetic biology holds great potential for expanding this list of microbially produced compounds even further. Yet embedding a novel biochemical pathway in the metabolic network of a host cell or modifying the expression of enzymes in a native biochemical pathway can disrupt the subtle regulatory mechanisms that the cell has evolved over millennia. Indeed, the final yield of a compound is often limited by deleterious effects on the engineered cell's metabolism that are difficult to predict due to limited understanding of the complex interactions that occur within the cell. The unregulated consumption of cellular resources, metabolic burden of heterologous protein production, and accumulation of pathway intermediates/products that are inhibitory or toxic to the host are all significant issues that may limit overall yield.

The concept of metabolic engineering which can be defined as purposeful modification of metabolic and cellular networks by employing various experimental techniques to achieve desired goals has emerged to fulfill this purpose. What distinguishes metabolic engineering from genetic engineering and strain improvement is that it considers metabolic and other cellular networks to identify targets to be engineered. In this sense, metabolic flux is an essential concept in the practice of metabolic engineering. Although gene expression levels and the concentrations of proteins and metabolites in the cell can provide clues to the status of the metabolic network, they have inherent limitations in fully describing the cellular phenotype due to the lack of information on the correlations among these cellular components. Metabolic fluxes represent the reaction rates in metabolic pathways and serve to integrate these factors through a mathematical framework. Thus, metabolic fluxes can be considered as one way of representing the phenotype of the cell as a result of interplays among various cell components; the observed metabolic flux profiles reflect the consequences of interconnected transcription, translation, and enzymatic reactions incorporating complex regulations.

Cell-free synthesis offers advantages over in vivo production methods. Cell-free systems can direct most, if not all, of the metabolic resources of the cell towards the exclusive production from one pathway. Moreover, the lack of a cell wall in vitro is advantageous since it allows for control of the synthesis environment. The redox potential, pH, or ionic strength can also be altered with greater flexibility than in vivo since one is not concerned about cell growth or viability. Furthermore, direct recovery of products can be easily achieved.

SUMMARY OF THE INVENTION

Compositions and methods are provided for controlling metabolic pathway flux through manipulation of targeted enzymes involved in a pathway of interest, including manipulation to maintain or alter the cellular concentration of key pathway enzymes during a cell growth phase, followed by manipulation to (a) increase concentrations of key pathway enzymes and/or (b) decrease concentrations of competitive enzymes during a production phase, wherein the product of the pathway of interest is produced. The cell growth phase involves intact cells, while the production phase is generally performed with lysates of such cells. In particular, the present invention provides modified genetic sequences encoding one or more key enzymes in a pathway of interest to relocate the key enzyme to a cellular or extra-cellular compartment where it is not naturally located and where the key enzyme does not substantially participate in pathway flux of the intact cell when it is thus relocated, for example, the periplasmic space.

In some embodiments, genetic sequences encoding one or more key enzymes in a pathway of interest are modified to result in the relocation of one or more enzymes to a cellular or extra-cellular compartment other than the naturally occurring compartment, e.g. to a different extra-cytoplasmic compartment or secreted outside of the cell to the surrounding medium.

In specific embodiments the genetic sequences encoding one or more key enzymes in a pathway of interest are modified to encode a peptide sequence that provides for periplasmic targeting of the polypeptide, so as to relocate, or sequester, the enzyme in the periplasmic space of the cell. In some embodiments the modified pathway enzyme is a pathway entry enzyme, as defined herein. In other embodiments the modified pathway enzyme is a rate-limiting enzyme.

For most purposes the periplasmically targeted or otherwise relocated enzyme is over-expressed in the cell, relative to the expression level in a native cell, by operably linking the coding sequence to a high level constitutive or inducible promoter. In certain embodiments of the invention, a native copy of the targeted enzyme, or an isozyme of the targeted enzyme, is expressed in the cell at physiologically normal levels, e.g., from the native promoter. In some embodiments, enzymes in the pathway other than the targeted enzyme are over-expressed, i.e. expressed at levels greater than the physiologically normal level.

During the cell growth phase, the relocated enzyme, which may be sequestered in the periplasm, for example, does not affect the pathway flux. In order to initiate the production phase, the cells are lysed, at which point the relocated enzyme is joined with the cytoplasmic enzymes in the pathway of interest, allowing high level production of the product of interest.

In some embodiments, methods are provided for producing a product of interest at a high flux rate, the method comprising: growing cells that are genetically modified to overexpress at least one relocated enzyme in a pathway of interest to a desired cell density; lysing the cells; and producing the product of the pathway in a cell-free system comprising the lysate. One or more substrates, nutrients, cofactors, buffers, reducing agents, and/or ATP generating systems, may be added to the cell-free system.

In another aspect, a genetically modified cell that over-expresses at least one relocated enzyme in a pathway of interest is provided.

In yet another aspect, lysates of such a genetically modified cell are provided, which lysate may be combined with one or more of substrates, nutrients, cofactors, buffers, reducing agents, and/or ATP generating systems, to generate a cell-free system for producing a product of interest.

The details of one or more embodiments of the invention are set forth herein. Other features, objects, and advantages of the invention will be apparent from the description, the figures, the examples, and the claims.

DETAILED DESCRIPTION OF CERTAIN EMBODIMENTS OF THE INVENTION

Figure 1:
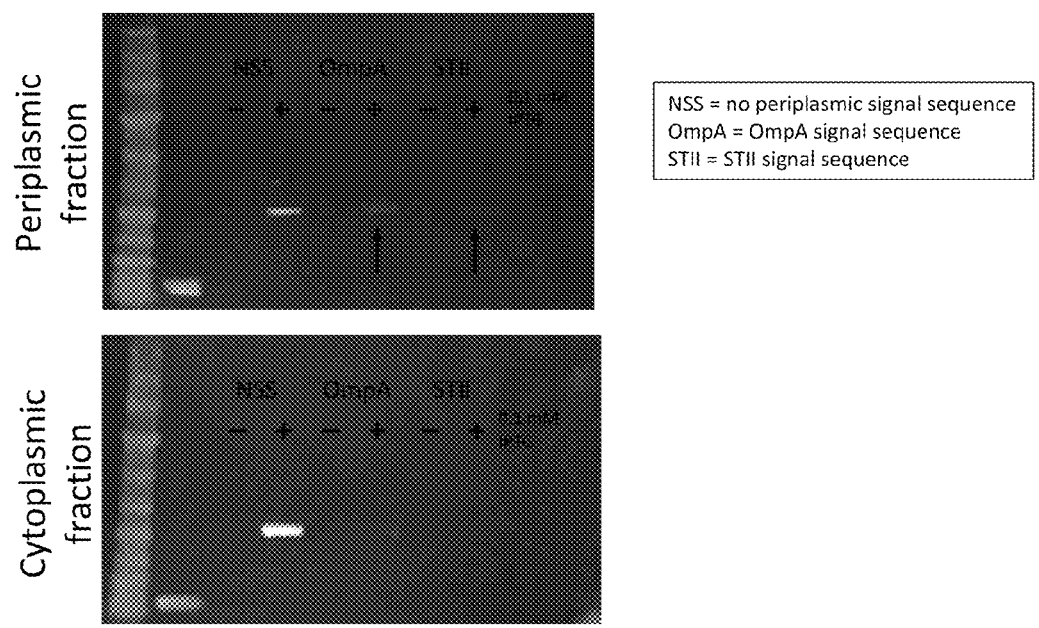
FIG. 1 illustrates the periplasmic localization of genetically modified AroG.

The present invention is based on the idea that genetically manipulated cells can be engineered to produce a functional element (e.g., an enzyme) that would have a negative impact on the health of the cell but for the relocation of that functional element outside of the cell or in a sequestered location within the cell. In one embodiment, such a sequestered location is the periplasmic space of the cell. In certain embodiments, the functional element is a key enzyme that controls flux in a pathway of interest.

For example, in one aspect, provided is a cell with at least one enzyme that controls flux in a pathway of interest, wherein the enzyme is genetically modified to relocate the key enzyme to a non-naturally occurring cellular or extra-cellular compartment (i.e., a cellular or extra-cellular compartment other than the compartment in which the enzyme naturally occurs), and wherein the enzyme does not participate in pathway flux of the intact cell when thus relocated. Exemplary pathways of interest include, but are not limited to, the syntheses of shikimate, various isoprenoids and terpenoids, poly-3-hydroxybutyrate, isobutanol, and 1-butanol, as detailed herein.

In certain embodiments, the enzyme is genetically modified to include a peptide sequence that provides for periplasmic targeting of the polypeptide, that is where the enzyme is sequestered in the periplasm of the cell. In certain embodiments, the enzyme is a pathway entry enzyme. In certain embodiments, the enzyme is a rate limiting enzyme. In certain embodiments, the enzyme increases the rate of precursor supply to the pathway of interest or supplies any other required substrate or cofactor. In certain embodiments, a native counterpart of the enzyme is expressed at normal cytoplasmic levels. In certain embodiments, the native counterpart is knocked out. In certain embodiments, the enzyme is over-expressed in the cell. In certain embodiments, the enzyme is present on either an episomal vector or a chromosome. In certain embodiments, at least two enzymes (e.g., two, three, four, five, or more enzymes) in the pathway of interest are genetically modified to comprise a peptide sequence that provides for periplasmic targeting of the polypeptide. In certain embodiments, the cell growth medium has been modified by the addition or enhancement of a factor (e.g., a nutrient, co-factor, reducing agent) that increases or preserves the activity of the enzyme.

In another aspect, provided is a system for producing a product of a pathway of interest, the system comprising a cell of the present invention; and optionally one or more substrates, enzymes, nutrients, co-factors, buffers, reducing agents, and ATP generating systems. In another aspect, provided is a system for producing a product of a pathway of interest, the system comprising a lysate of a cell of the present invention; and optionally one or more substrates, enzymes, nutrients, co-factors, buffers, reducing agents, and ATP generating systems. In certain embodiments, the system further includes one or more additional cell lysates.

In yet another aspect, provided is a method of producing a product of a pathway of interest, the method comprising growing a cell of the present invention to a desired cell density; lysing the cells; and combining the lysate with one or more substrates, enzymes, nutrients, co-factors, buffers, reducing agents, or ATP generating systems, wherein the enzymes in the pathway of interest cause production of the desired product. In certain embodiments, the method further comprises combining the lysate with one or more additional cell lysates.

In yet another aspect, provided is a vector that encodes an enzyme genetically modified to comprise a peptide sequence that provides for periplasmic targeting of the polypeptide.

Periplasmic Sequestration

In some embodiments of the invention, enzyme relocation is to the periplasmic space. In such aspects, the present invention provides for methods of generating cells; lysates; and uses thereof, in which one or more key enzymes in a pathway of interest are genetically modified to incorporate a peptide sequence that provides for periplasmic targeting of the polypeptide. Periplasmic targeting signal peptide sequences (also called targeting signals or signal sequences) usually are found on the N-terminus of bacterial secretory proteins. They vary in length from about 15 to about 70 amino acids. The primary amino acid sequences of the signal peptides also vary, but generally have a common overall structure including the following parts: i) the N-terminal part has a variable length and generally carries a net positive charge; ii) following is a central hydrophobic core of about 6 to about 15 amino acids; and iii) the final part includes four to six amino acids which define the cleavage site for signal peptidases.

Periplasmic targeting signal peptide sequences suitable for use in the present invention are generally derived from a protein that is secreted in a Gram negative bacterium. The secreted protein may be encoded by the bacterium, or by a bacteriophage that infects the bacterium. Examples of suitable Gram negative bacterial sources of secreted proteins include, but are not limited to, members of the genera *Escherichia, Pseudomonas, Klebsiella, Salmonella, Caulobacter, Methylomonas, Acetobacter, Achromobacter, Acinetobacter, Aeromonas, Agrobacterium, Alcaligenes, Azotobacter, Burkholderia, Citrobacter, Comamonas, Enterobacter, Erwinia, Rhizobium, Vibrio,* and *Xanthomonas.*

There are three pathways for translocation across the cytoplasmic membrane: (i) SecB-dependent, (ii) signal recognition particle (SRP), and (iii) twin arginine translocation (TAT) pathways. SecB-dependent and signal recognition particle pathways both use the SecYEG translocon. The twin arginine translocation pathway uses the TatABCE complex. SecB-dependent translocation is most commonly used, but this pathway is not able to transport folded proteins. Rapid cytoplasmic folding may necessitate use of SRP or TAT pathways. Examples of bacterial secreted proteins having periplasmic targeting signal peptides include, but are not limited to, proteins encoded by the following genes: ompA, geneIII, *E. coli* alkaline phosphatase, lamB, malE, secE, secY, and prlA-4. One skilled in the art can easily identify the periplasmic targeting signal peptide located at the N-terminus of each of these proteins, and of other bacterial secretory proteins. It is also known by one skilled in the art that some amino acid substitutions, additions, and/or deletions may be made in a periplasmic targeting signal peptide while retaining its targeting function. Thus a functional periplasmic targeting signal peptide of use in the instant invention may be fully natural or a modified sequence.

The steps in the process of periplasmic sequestration include: i) pathway analysis to identify a key entry enzyme(s) for sequestration to the periplasm, ii) construction of expression cassettes for periplasmic targeting of the enzyme(s) including signal peptide selection and expression optimization, iii) verification of active, periplasmically-expressed target enzyme, and iv) demonstration of metabolically healthy cell growth followed by increased flux to the product of interest post-lysis in an active, cell-free reaction.

The fusion proteins of the present invention comprise a periplasmic targeting signal (PerS) and a pathway enzyme, e.g. a pathway entry enzyme and/or a rate-limiting enzyme. Generally the optimal periplasmic signal peptide for each protein targeted to periplasm is empirically determined from a selection of such peptides. The efficiency of secretion will depend on various parameters, e.g., the signal peptide used, the protein being targeted, host strain used, and/or expression level. For example, a library of modified genes with varying 5' regions coding for different periplasmic signal peptides can be created using PCR or other methods familiar to those skilled in the art. This library is subcloned in a vector enabling controlled expression (e.g., a vector enabling controlled expression using the T7 induction system such as a vector from the pET series), and tested for export efficiency as well as target protein activity (see, e.g., Dahl et al., *J. Biol. Chem.* (1992) 267:4882-4888; Chen et al., *J. Biol. Chem.* (1992) 267:12375-12379; U.S. Publication No. 2007/0111283; Mergulhao et al., *J. Microbiol. Biotechnol.* (2007) 17:1236-1241; and Mergulhao et al., *Biotechnology Advances* (2005) 23:177-202, each incorporated herein by reference). Exemplary periplasmic targeting signals are included, without limitation, in Table 1.

TABLE 1

Periplasmic TargetingSignals

| Name | Signal peptide | Pathway | Source |
|---|---|---|---|
| MalEss | MKIKTGARILALSALTTMMFSASALA (SEQ ID NO: 1) | Sec | E. coli |
| PhoAss | MKQSTIALALLPLLFTPVTKA (SEQ ID NO: 2) | Sec | E. coli |
| LamBss | MMITLRKLPLAVAVAAGVMSAQAMA (SEQ ID NO: 3) | Sec | E. coli |
| MglBss | MNKKVLTLSAVMASMLFGAAAHA (SEQ ID NO: 4) | Sec | E. coli |
| PelBss | MKYLLPTAAAGLLLLAAQPAMA (SEQ ID NO: 5) | Sec | E. caratovora |
| DsbAss | MKKIWLALAGLVLAFSASA (SEQ ID NO: 6) | SRP | E. coli |
| SfmCss | MMTKIKLLMLIIFYLIISASAHA (SEQ ID NO: 7) | SRP | E. coli |
| TolBss | MKQALRVAFGFLILWASVLHA (SEQ ID NO: 8) | SRP | E. coli |
| TorTss | MRVLLFLLLSLFMLPAFS (SEQ ID NO: 9) | SRP | E. coli |
| TorAss | MANNDLFQASRRRFLAQLGGLTVAGMLGPSLLTPRRATA (SEQ ID NO: 10) | TAT | E. coli |

Tables 4 and 5 of the Examples provide exemplary primers useful in incorporating one of the sequences of Table 1 at the N-terminus of a protein of interest, and includes sequences for restriction sites useful in subcloning. It is understood that one skilled in the art would be able to encode a periplasmic targeting signal, as exemplified in Table 1, using nucleic acid sequences different than those exemplified in Tables 4 and 5 based on the degenerate nature of the genetic code. Silent mutations in the nucleic acid sequence (i.e., not affecting the amino acid sequence) will not affect periplasmic targeting activity. Non-silent mutations in the nucleic acid sequence (i.e., affecting the amino acid sequence) are also possible which would not substantially affect periplasmic targeting. In certain embodiments, one, two, three, four, or five mutations in a periplasmic targeting signal of Table 1 achieves targeting to the periplasm. In certain embodiments, at least 90%, 95%, 98%, or 99% homology in an amino acid sequence of Table 4 and/or 5 achieves targeting to the periplasm of the protein of interest. In certain embodiments, the codon usage in the nucleic acid sequence encoding the periplasmic targeting signal is optimized for the host organism.

A cleavage site is optionally located between the periplasmic targeting signal (PerS) and the enzyme to allow separation of these peptides. The cleavage site may be any site that can be used in separating the PerS and the enzyme. Any cleavage site making use of any method for protein cleavage may be used. PerS from *E. coli* may contain within their signal sequence a motif recognized by leader peptidase (Lep) for signal sequence processing and cleavage. Other methods that may find use include protease cleavage methods, e.g.

thrombin, factor Xa protease, and other endo peptidases, such as trypsin. The genes encoding the fusion protein can be synthesized to include a cleavage site for one of these proteases between the PerS peptide and the enzyme sequence. Another system for fusion and cleavage is the intein/chitin binding domain system which makes use of the self cleaving properties of intein proteins (see, e.g., Chong et al., *Gene* (1997) 192:271-281).

DNA sequences encoding periplasmic targeting signals useful in the invention may be the natural coding sequences present in the genes from which they are derived. Additionally, the encoding sequence may be back-translated using the amino acid sequence of the periplasmic targeting signal, optionally using optimized codons. A DNA fragment encoding a periplasmic targeting signal that is used in a fusion protein encoding isolated nucleic acid fragment may be obtained using any method such as isolation from nature, chemical synthesis, recombinant techniques, or amplification such as by using PCR.

Nucleic Acids, Polypeptides, and Cells for Use in the Present Invention

The nucleic acids used to practice this invention, whether RNA, iRNA, antisense nucleic acid, cDNA, genomic DNA, vectors, artificial chromosomes, viruses, or hybrids thereof may be isolated from a variety of sources, genetically engineered, amplified, and/or expressed/generated recombinantly. A nucleic acid molecule or nucleic acid molecules that encode any of the enzymes associated with the invention can be introduced into a cell or cells using methods and techniques that are standard in the art. For example, nucleic acid molecules can be introduced by standard protocols such as transformation including chemical transformation and electroporation, transduction, particle bombardment, etc. Expressing a nucleic acid molecule(s) encoding an enzyme also may be accomplished by integrating the nucleic acid molecule into the genome. Nucleic acid molecule(s) can be integrated into a cell's genomic DNA using standard techniques well known in the art. Recombinant polypeptides generated from these nucleic acids can be individually isolated or cloned and tested for a desired activity. Any recombinant expression system can be used, including, but not limited to, bacterial, mammalian, yeast, insect, or plant cell expression systems. The nucleic acids for use in the present invention can be synthesized in vitro by well-known chemical synthesis techniques, as described in, e.g., Adams et al., *J. Am. Chem. Soc.* (1983) 105:661; Belousov et al., *Nucleic Acids Res.* (1997) 25:3440-3444; Frenkel et al., *Free Radic. Biol. Med.* (1995) 19:373-380; Blommers et al., *Biochemistry* (1994) 33:7886-7896; Narang et al., *Meth. Enzymol.* (1979) 68:90; Brown et al., *Meth. Enzymol.* (1979) 68:109; Beaucage et al., *Tetrahedron Letters* (1981) 22:1859; and U.S. Pat. No. 4,458,066, each of which is incorporated herein by reference.

Host cells of interest for pathway engineering include a wide variety of heterotrophic and autotrophic microorganisms, including, but not limited to, bacteria, fungi and protozoans. Preferred host cells include those for which means by which a polypeptide can be directed to a cellular compartment or extracellular compartments are known. The invention encompasses any type of cell that recombinantly expresses nucleic acids associated with the invention, including prokaryotic and eukaryotic cells. In some embodiments the cell is a bacterial cell, such as *Escherichia* spp., *Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp. and *Pantoea* spp. The bacterial cell can be a Gram-negative cell such as an *Escherichia coli* (*E. coli*) cell, or a Gram-positive cell such as a species of *Bacillus*. In other embodiments the cell is a fungal cell such as yeast cells, e.g., *Saccharomyces* spp., *Schizosaccharomyces* spp., *Pichia* spp., *Paffia* spp., *Kluyveromyces* spp., *Candida* spp., *Talaromyces* spp., *Brettanomyces* spp., *Pachysolen* spp., *Debaryomyces* spp., *Yarrowia* spp. and industrial polyploid yeast strains. Other non-limiting examples of fungi include *Aspergillus* spp., *Pennicilium* spp., *Fusarium* spp., *Rhizopus* spp., *Acremonium* spp., *Neurospora* spp., *Sordaria* spp., *Magnaporthe* spp., *Allomyces* spp., *Ustilago* spp., *Botrytis* spp., and *Trichoderma* spp. In other embodiments the cell is an algal cell, a plant cell, or a mammalian cell. It should be appreciated that some cells compatible with the invention may express an endogenous copy of one or more of the genes associated with the invention as well as a recombinant copy. Species of interest include, without limitation, *S. cerevisiae*, *E. coli*, *Pseudomonas* species, *Klebsiella* species, and *Synechocystis* species. To avoid unwanted degradation of the relocated protein, the host strain can be modified to remove various compartmental proteases (e.g. periplasmic proteases) and/or to augment with proteins such as chaperones and maturases to assist with protein folding; such modifications and augmentations employ methods familiar to those skilled in the art; see, e.g., U.S. Pat. Nos. 4,946,783 and 6,921,659, and Chen et al., *Biotechnology and Bioengineering* (2004) 85: 463-474, each of which is incorporated herein by reference.

In some embodiments one or more genes associated with the invention is expressed recombinantly in a bacterial cell. Bacterial cells according to the invention can be cultured in media of any type (rich or minimal) and any composition. In some embodiments, the cells are culture in minimal medium. As would be understood by one of ordinary skill in the art, routine optimization would allow for use of a variety of types of media. The selected medium can be supplemented with various additional components. Some non-limiting examples of supplemental components include glucose, antibiotics, IPTG, tetracycline or anhydro-tetracycline (aTc) for gene induction and ATCC Trace Mineral Supplement. Similarly, other aspects of the medium, and growth conditions of the cells of the invention may be optimized through routine experimentation. For example, pH and temperature are non-limiting examples of factors which can be optimized. In some embodiments the concentration and amount of a supplemental component may be optimized. In some embodiments, how often the media is supplemented with one or more supplemental components, and the amount of time that the media is cultured is optimized.

Techniques for the manipulation of nucleic acids, e.g., subcloning, labeling probes (e.g., random-primer labeling using Klenow polymerase, nick translation, amplification), sequencing, hybridization and the like are well described in the scientific and patent literature, see, e.g., Sambrook, Ed., *Molecular Cloning: A Laboratory Manual* ($2^{nd}$ Ed.) Vols 1-3, Cold Spring Harbor Laboratory (1989); Ausubel, Ed., *Current Protocols in Molecular Biology*, John Wiley & Sons, Inc., New York (1997); and Tijssen, Ed., *Laboratory Techniques in Biochemistry and Molecular Biology: Hybridization with Nucleic Acid Probes, Part I. Theory and Nucleic*

*Acid Preparation*, Elsevier, N.Y. (1993), each of which is incorporated herein by reference.

It should be appreciated that the genes encoding enzymes associated with the invention can be obtained from a variety of sources. As one of ordinary skill in the art would be aware, homologous genes for these enzymes exist in many species and can be identified by homology searches, for example through a protein BLAST search, available at the NCBI internet site (www.ncbi.nlm.nih.gov). Genes encoding for these enzymes can be PCR amplified from DNA from any source which contains the given enzyme, for example using degenerate primers, as would be understood by one of ordinary skill in the art. In some embodiments, the gene encoding for a given enzyme can be synthetic. Any means of obtaining the genes encoding for the enzymes discussed here are compatible with aspects of the instant invention.

The invention also provides isolated polypeptides encoded by the nucleic acids. Such polypeptides are useful, for example, alone or as fusion proteins. Polypeptides associated with the invention can be isolated from biological samples including tissue or cell homogenates, and can also be expressed recombinantly in a variety of prokaryotic and eukaryotic expression systems by constructing an expression vector appropriate to the expression system, introducing the expression vector into the expression system, and isolating the recombinantly expressed protein. Polypeptides can also be synthesized chemically using well-established methods of peptide synthesis.

A variety of methodologies well-known to the skilled practitioner can be utilized to obtain isolated polypeptides associated with the invention. The polypeptide may be purified from cells which naturally produce the polypeptide by chromatographic means or immunological recognition. Alternatively, an expression vector may be introduced into cells to cause production of the polypeptide. In another method, mRNA transcripts may be microinjected or otherwise introduced into cells to cause production of the encoded polypeptide. Translation of mRNA in cell-free extracts such as the reticulocyte lysate system also may be used to produce polypeptide. Those skilled in the art also can readily follow known methods for isolating polypeptides. These include, but are not limited to, immunochromatography, HPLC, size-exclusion chromatography, ion-exchange chromatography and immune-affinity chromatography.

The expression of the molecules of the invention may be determined using routine methods known to those of ordinary skill in the art. These methods include, but are not limited to: direct RNA amplification, reverse transcription of RNA to cDNA, real-time RT-PCR, amplification of cDNA, hybridization, and immunologically based assay methods, which include, but are not limited to immunohistochemistry, antibody sandwich capture assay, ELISA, and enzyme-linked immunospot assay (EliSpot assay). For example, the determination of the presence of level of nucleic acid molecules of the invention in a subject or tissue can be carried out via any standard nucleic acid determination assay, including the polymerase chain reaction, or assaying with labeled hybridization probes. Such hybridization methods include, but are not limited to microarray techniques.

The invention thus involves in one aspect enzymes, genes encoding those enzymes, functional modifications and variants of the foregoing, as well as uses relating thereto. Homologs and alleles of the nucleic acids of the invention can be identified by conventional techniques. Also encompassed by the invention are nucleic acids that hybridize under stringent conditions to the nucleic acids described herein. The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$(pH7), 0.5% SDS, 2 mM EDTA). SSC is 0.15M sodium chloride/0.015M sodium citrate, pH7; SDS is sodium dodecyl sulphate; and EDTA is ethylenediaminetetracetic acid. After hybridization, the membrane upon which the DNA is transferred is washed, for example, in 2×SSC at room temperature and then at 0.1-0.5×SSC/0.1× SDS at temperatures up to 68° C.

There are other conditions, reagents, and so forth which can be used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of nucleic acids of the invention (e.g., by using lower stringency conditions). The skilled artisan also is familiar with the methodology for screening cells and libraries for expression of such molecules which then are routinely isolated, followed by isolation of the pertinent nucleic acid molecule and sequencing.

In general, homologs and alleles typically will share at least 75% nucleotide identity and/or at least 80% amino acid identity to the sequences of nucleic acids and polypeptides, respectively, in some instances will share at least 90% nucleotide identity and/or at least 90 or 95% amino acid identity and in still other instances will share at least 95% nucleotide identity and/or at least 99% amino acid identity. In some embodiments, homologs and alleles will share at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% nucleotide identity to the sequences of nucleic acids and/or 80%, 81%, 82%, 83%, 84%, 85%, 86%, 87%, 88%, 89%, 90%, 91%, 92%, 93%, 94%, 95%, 96%, 97%, 98%, or 99% identity to the sequences of polypeptides.

The homology can be calculated using various, publicly available software tools developed by NCBI (Bethesda, Md.) that can be obtained through the NCBI internet site. Exemplary tools include the BLAST software, also available at the NCBI internet site (www.ncbi.nlm.nih.gov). Pairwise and ClustalW alignments (BLOSUM30 matrix setting) as well as Kyte-Doolittle hydropathic analysis can be obtained using the MacVector sequence analysis software (Oxford Molecular Group). Watson-Crick complements of the foregoing nucleic acids also are embraced by the invention.

In screening for and identifying genes, techniques known to those of ordinary skill in the art such as Southern blots, Northern blots and amplification protocols such as polymerase chain reaction using primers which hybridize to the sequences presented can be applied.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code. The invention also embraces codon optimization to suit optimal codon usage of a host cell.

The invention also provides modified nucleic acid molecules which include additions, substitutions and deletions of one or more nucleotides. In preferred embodiments, these modified nucleic acid molecules and/or the polypeptides they encode retain at least one activity or function of the unmodified nucleic acid molecule and/or the polypeptides, such as enzymatic activity. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art.

For example, modified nucleic acid molecules which encode polypeptides having single amino acid changes can be prepared. Each of these nucleic acid molecules can have one, two or three nucleotide substitutions exclusive of nucleotide changes corresponding to the degeneracy of the genetic code as described herein. Likewise, modified nucleic acid molecules which encode polypeptides having two amino acid changes can be prepared which have, e.g., 2-6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions which code for the amino acid substitutions. Additional nucleic acid molecules that encode polypeptides having additional substitutions (i.e., 3 or more), additions or deletions (e.g., by introduction of a stop codon or a splice site(s)) also can be prepared and are embraced by the invention as readily envisioned by one of ordinary skill in the art. Any of the foregoing nucleic acids or polypeptides can be tested by routine experimentation for retention of structural relation or activity to the nucleic acids and/or polypeptides disclosed herein.

The invention embraces variants of the polypeptides described herein. As used herein, a "variant" of a polypeptide is a polypeptide which contains one or more modifications to the primary amino acid sequence of the polypeptide. Modifications which create an enzyme variant can be made to an enzyme, for example, 1) to alter the cellular distribution of the enzyme; 2) to reduce or eliminate an activity of the enzyme; 3) to enhance a property of an enzyme, protein stability in an expression system or the stability of protein-protein binding; 4) to provide a novel activity or property to an enzyme, such as addition of an antigenic epitope or addition of a detectable moiety; or 5) to provide equivalent or better binding between an enzyme and an enzymatic substrate.

Modifications to a polypeptide are typically made to the nucleic acid which encodes the polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins. One of skill in the art will be familiar with methods for predicting the effect on protein conformation of a change in protein sequence, and can thus "design" a variant polypeptide according to known methods. One example of such a method is described by Dahiyat and Mayo in *Science* 278:82-87, 1997, whereby proteins can be designed de novo. The method can be applied to a known protein to vary a only a portion of the polypeptide sequence. By applying the computational methods of Dahiyat and Mayo, specific variants of a polypeptide can be proposed and tested to determine whether the variant retains a desired conformation.

In general, variants include polypeptides which are modified specifically to alter a feature of the polypeptide unrelated to its desired physiological activity. For example, cysteine residues can be substituted or deleted to prevent unwanted disulfide linkages. Similarly, certain amino acids can be changed to enhance expression of a polypeptide by eliminating proteolysis by proteases in an expression system (e.g., dibasic amino acid residues in yeast expression systems in which KEX2 protease activity is present).

Mutations of a nucleic acid which encode a polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a gene or cDNA clone to enhance expression of the polypeptide. The activity of variants of polypeptides can be tested by cloning the gene encoding the variant polypeptide into a bacterial or mammalian expression vector, introducing the vector into an appropriate host cell, expressing the variant polypeptide, and testing for a functional capability of the polypeptides as disclosed herein.

The skilled artisan will also realize that conservative amino acid substitutions may be made in polypeptides to provide functionally equivalent variants of the foregoing polypeptides, i.e., the variants retain the functional capabilities of the polypeptides. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g., *Molecular Cloning: A Laboratory Manual*, J. Sambrook, et al., eds., Second Edition, Cold Spring Harbor Laboratory Press, Cold Spring Harbor, N.Y., 1989, or *Current Protocols*

*in Molecular Biology*, F. M. Ausubel, et al., eds., John Wiley & Sons, Inc., New York. Exemplary functionally equivalent variants of the polypeptides include conservative amino acid substitutions in the amino acid sequences of proteins disclosed herein. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In general, it is preferred that fewer than all of the amino acids are changed when preparing variant polypeptides. Where particular amino acid residues are known to confer function, such amino acids will not be replaced, or alternatively, will be replaced by conservative amino acid substitutions. Preferably, 1, 2, 3, 4, 5, 6, 7, 8, 9, 10, 11, 12, 13, 14, 15, 16, 17, 18, 19, 20 residues can be changed when preparing variant polypeptides. It is generally preferred that the fewest number of substitutions is made. Thus, one method for generating variant polypeptides is to substitute all other amino acids for a particular single amino acid, then assay activity of the variant, then repeat the process with one or more of the polypeptides having the best activity.

Conservative amino-acid substitutions in the amino acid sequence of polypeptides to produce functionally equivalent variants of polypeptides typically are made by alteration of a nucleic acid encoding a polypeptide. Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* (1985) 82: 488-492), or by chemical synthesis of a gene encoding a polypeptide.

Vectors and Expression Constructs for Use in the Present Invention

Vectors useful for the transformation of an isolated DNA fragment encoding a fusion protein of the present invention into suitable host cells are well known in the art. As used herein, a "vector" may be any of a number of nucleic acids into which a desired sequence or sequences may be inserted by restriction and ligation for transport between different genetic environments or for expression in a host cell. Vectors are typically composed of DNA, although RNA vectors are also available. Vectors include, but are not limited to: plasmids, fosmids, phagemids, virus genomes and artificial chromosomes. Typically the vector contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment that controls transcriptional termination. Vectors may also be used which promote the integration of the chimeric gene encoding a fusion protein of the invention into the host cell genome. Such vectors may be for random integration, site-directed integration, or for homologous recombination. A vector may have features allowing single cross-over or double-crossover types of homologous recombination. One or multiple copies may be integrated into a host cell genome.

A cloning vector is one which is able to replicate autonomously or integrated in the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript can be translated into the desired protein or polypeptide.

When the nucleic acid molecule that encodes any of the enzymes of the claimed invention is expressed in a cell, a variety of transcription control sequences (e.g., promoter/enhancer sequences) can be used to direct its expression. The promoter can be a native promoter, i.e., the promoter of the gene in its endogenous context, which provides normal regulation of expression of the gene. In some embodiments the promoter can be constitutive, i.e., the promoter is unregulated allowing for continual transcription of its associated gene. A variety of conditional promoters also can be used, such as promoters controlled by the presence or absence of a molecule.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (or RNA). That heterologous DNA (or RNA) is placed under operable control of transcriptional elements to permit the expression of the heterologous DNA in the host cell. In some embodiments two or more of the nucleic acids of the invention may be cloned into the same expression vector or plasmid.

The methods of the invention may make use of constitutive or regulated expression of various coding sequences. Expression may be regulated by various cues, for example, induction by chemicals, change of growth phase, depletion of a nutrient, temperature shifts, and/or light. In some embodiments, inducible promoters are regulated by the presence of an inducing agent, for example, a chemical such as lactose, arabinose, or tetracycline, as known in the art. Typically where "high level" expression is indicated, the concentration of the expressed protein in the cell is at least about 2-fold above basal levels; at least about 10-fold above basal levels; at least about 25-fold above basal levels; at least about 50-fold above basal levels; or more, e.g., between about 2-fold to about 100-fold above basal levels.

Expression and cloning vectors usually contain a promoter that is recognized by the host organism and is operably linked to the coding sequence of interest. Promoters are untranslated sequences located upstream (5') to the start codon of a structural gene that control the transcription of a particular nucleic acid sequence to which they are operably linked. Such promoters typically fall into two classes: inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known, e.g., for *E. coli* see, e.g., Hawley and McClure Nucleic Acids Res. (1983) 11:2237-55; for *B. subtilis* see, e.g., Ishii et al., *Nucleic Acids Res.* (2001) 29:278-280; for *Saccharomyces cerevisiae* see, e.g., Chang et al., *Nucleic Acids Res*. (2011) 39:D647-52. See also Madigan, Martinko, and Parker, eds., *Brock Biology of Microorganisms*. 9$^{th}$ Ed. Prentice Hall. Upper Saddle River, N.J. While the native promoter may be used, for most purposes heterologous promoters are preferred, as they generally permit greater transcription and higher yields.

Promoters suitable for use with prokaryotic hosts include the □-lactamase and lactose promoter systems, alkaline phosphatase, a tryptophan (trp) promoter system, and numerous hybrid promoters such as the tac promoter. However, other known bacterial or bacteriophage promoters are also suitable, e.g. the laI promoter, the lacZ promoter, the T3 promoter, the T7 promoter, the arabinose promoter, the gpt promoter, the lambda PR promoter, the lambda PL promoter, promoters from operons encoding glycolytic enzymes such as 3-phosphoglycerate kinase (PGK), and the acid phosphatase promoter. Their nucleotide sequences have been published, thereby enabling one of skill in the art to operably ligate them to a sequence of interest using linkers or adapters. Promoters for use in bacterial systems also will contain a Shine-Dalgarno (S.D.) sequence operably linked to the coding sequence (see, e.g., Shine and Dalgarno, *Nature* (1975) 254: 34-8; Madigan, Martinko, and Parker, eds., *Brock Biology of Microorganisms*. 9$^{th}$ Ed. Prentice Hall. Upper Saddle River, N.J.). In certain cases, also, the host cell may be modified genetically to adjust concentrations of metabolite or inducer transporter proteins so that all cells in a culture will be induced equivalently.

Promoters suitable for eukaryotic cells, e.g. yeast cells, are also known in the art. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the polyA tail to the 3' end of the coding sequence. All of these sequences are suitably inserted into eukaryotic expression vectors. Examples of suitable promoting sequences for use with yeast hosts include the promoters for 3-phosphoglyceratekinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription being controlled by growth conditions, are the promoter regions for alcohol dehydrogenase 2, isocytochrome C, acid phosphatase, degradative enzymes associated with nitrogen metabolism, metallothionein, and enzymes responsible for maltose and galactose utilization. Yeast enhancers also are advantageously used with yeast promoters.

It may be desirable to experimentally adjust expression rate to optimize efficiency of export. Poor translocation can result from insufficient capacity of export machinery. Methods for adjustment of expression rate include, without limitation, modification of copy number of the plasmid carrying the gene coding for the protein to be exported to the periplasm. Replicons known and used in the art include P15A (10 copies/cell), ColA (30 copies/cell), ColE1 (40 copies/cell), and RSF1030 (>100 copies/cell). The ribosome binding site in the 5' UTR of the gene coding for the protein to be exported to the periplasm may be modified, where a library of ribosome binding sites with varying strengths can be created and tested; see, e.g., Salis et al., *Nature Biotechnology* (2009) 27: 946-950; and Simmons et al., *Nature Biotechnology* (1996) 14:629-634, each incorporated herein by reference. The promoter region upstream of the gene coding for the protein to be exported may be modified to adjust the rate of transcription, where a library of promoter regions with varying strengths can be created and tested; see, e.g., Alper et al., PNAS (2005) 102:12678-12683; and De Mey et al., *BMC Biotechnology* (2007) 7:34, each of which is incorporated herein by reference.

Metabolic Flux

"Flux" or "metabolic flux" refers to the rate that molecules pass through a pathway or reaction of interest. Among the factors that control flux are rate of catalysis of enzymes in the pathway, the availability of substrate, the concentration of enzymes in a cell, and/or the proximity of enzymes in a pathway.

While a high rate of flux through a pathway of interest is desirable, at the same time it can create toxicity issues if a product not normally accumulated at high levels in the cell is produced at a high rate relative to that occurring under normal conditions. It is understood that a high rate of flux is pathway specific, and refers to the concentration of pathway product over time, such as, for example, production of a product at a rate of about 0.1 to about 20 grams of product/L/h.

A stressed cell produces a number of proteins undesirable for maintaining active biocatalysis, such as nucleases, heat shock proteins, proteases and the like.

The methods of the invention provide a means of controlling flux through a pathway, such that a healthy cell (e.g., with substantially normal physiology) can be grown to high density (e.g., for example, from about 30 to about 300 $OD_{550}$) during which time period the concentration of enzymes involved in a desired pathway are increased without resulting in a deleterious (to cell health) increase in the pathway flux or toxic accumulation of metabolic products. $OD_{550}$ refers to the optical density at 550 nm, wherein 1 $OD_{550}$ is about $10^9$ cells/mL (E. coli).

Methods of determining flux rates are known and used in the art; see, e.g., Wiechert et al., Metab. Eng. (2001) 3:265-283, and Wiechert et al., Metab. Eng. (2001)3:195-206; and metabolic engineering texts such as Lee and Papoutsakis, Eds., Metabolic Engineering, Marcel Dekker, Inc. N.Y. (1999); Stephanopoulos, Nielsen, and Aristidou, Eds., Metabolic Engineering: Principles and Methodology, Academic Press, New York (1998); Nielsen and Eggeling, Eds., Metabolic Engineering, Springer, London (2001), each of which is incorporated herein by reference. Flux may be calculated from measurable quantities using techniques such as metabolic flux analysis (MFA), for example by direct measurement of the conversion rate of isotopically labeled substrate.

Pathways of Interest

As used herein, the term "enzyme pathway" or "pathway of interest" refers to a cellular system for converting a substrate to a product of interest, where the system comprises a plurality of enzymes and may additionally comprise substrates acted upon by one or more of the enzymes, products of the enzyme-catalyzed reactions, co-factors utilized by the enzymes, and the like. The system may be present in an intact cell, or in a lysate of a cell. Many metabolic pathways are known and have been described in microbial systems, and are accessible in public databases; see, e.g., Smolke, Ed., The Metabolic Pathway Engineering Handbook: Tools and Applications, CRC Press, New York (2009); Stephanopoulos, Nielsen, and Aristidou, Eds., Metabolic Engineering Principles and Methodology, Academic Press, New York (1998); Greenberg, Metabolic Pathways: Energetics, Tricarboxylic Acid Cycle, and Carbohydrates, Academic Press, New York (1967); and D. M. Greenberg's multi-volume series entitled Metabolic pathways, Volumes 1-7, each of which is incorporated herein by reference.

Pathways of interest include, for example, pathways involved in carbohydrate, amino acid, nucleic acid, steroid, fatty acid, and natural product biosynthesis, and encompass the synthesis of various chemical compounds and materials, including, but not limited to:
  a) antibiotics; e.g., actinomycin, bleomycin, rifamycin, chloramphenicol, tetracycline, lincomycin, erythromycin, streptomycin, cyclohexamide, puromycin, cycloserine, bacitracin, penicillin, cephalosporin, vancomycin, polymyxin, and gramicidin;
  b) biosurfactants; e.g., rhamnolipids, sophorolipids, glycolipids, and lipopeptides;
  c) biological fuels; e.g., bioethanol, biodiesel, and biobutanol;
  d) amino acids; e.g., L-glutamate, L-lysine, L-phenylalanine, L-aspartic acid, L-isoleucine, L-valine, L-tryptophan, L-proline (hydroxyproline), L-threonine, L-methionine, and D-p-hydroxyphenylglycine;
  e) organic acids; e.g., citric acid, lactic acid, gluconic acid, acetic acid, propionic acid, succinic acid, fumaric acid, and itaconic acid;
  f) fatty acids; e.g., arachidonic acid, polyunsaturated fatty acid (PUBA), and γ-linoleic acid;
  g) alcohols and polyols; e.g., glycerol, mannitol, erythritol, xylitol, poly-3-hydroxybutyrate, isobutanol, and 1-butanol;
  h) flavors and fragrances; e.g., vanillin, benzaldehyde, dihydroxyacetone, 4-(R)-decanolide, and 2-actyl-1-pyrroline;
  i) nucleotides; e.g., 5'-guanylic acid and 5'-inosinic acid;
  j) vitamins; e.g., vitamin C, vitamin F, vitamin B2, provitamin D2, vitamin B12, folic acid, nicotinamide, biotin, 2-keto-L-gulonic acid, and provitamin Q10;
  k) pigments; e.g., astaxathin, β-carotene, lycopene, monascorubrin, and rubropunctatin;
  l) sugars and polysaccharides; e.g., ribose, sorbose, xanthan, gellan, and dextran; and
  m) biopolymers and plastics; e.g., polyhydroxyalkanoates (PHA), poly-γ-glutamic acid, and 1,3-propanediol.

Other examples of pathways of interest include the synthesis of various E. coli metabolites. A metabolite is any substance used or produced during metabolism (i.e., an enzyme, substrate, or product). For the purposes of the present invention, a metabolite is often, although not always, the product of an enzyme in the pathway of interest. Exemplary E. coli metabolites include, but are not limited to, 2,3-Dihydroxybenzoic acid, 2-Ketoglutarate, 3-Phosphoglycerate, 4-Hydroxybenzoate, 6-Phosphogluconate, Acetoacetyl-CoA, Acetyl-CoA, Acetylphosphate, Adenine, Adenosine, Adenosine phosphosulfate, ADP, ADP-glucose, Alanine, AMP, Anthranilate, Arginine, Asparagine, Aspartate, ATP, Carbamylaspartate, Cis-aconitate, Citrate, Citrulline, CMP, Coenzyme A, CTP, Cyclic AMP, Cytidine, Cytosine, dAMP, dATP, dCTP, Deoxyadenosine, Deoxyguanosine, Deoxyribose-5-P, dGMP, Dihydroorotate, Dihydroxyacetone phosphate, dTDP, dTTP, Eyrthrose-4-phosphate, FAD, Flavin mononucleotide, Fructose-1,6-bisphosphate, Fructose-6-phosphate, Fumarate, GDP, Gluconate, Gluconolactone, Glucosamine-6-phosphate, Glucose-6-phosphate, Glucose-1-phosphate, Glutamate, Glutamine, Glutathione, Glutathione disulfide, glyceraldehyde-3-phosphate, Glycerate, Glycerol-3-phosphate, GMP, GTP, Guanine, Guanosine, Histidine, Histidinol, Homocysteine, Inosine diphosphate, Inosine monophosphate, Inosine triphosphate, Isoleucine, Lysine, Malate, Malonyl-CoA, Methionine, Myo-inositol, N-Acetylglucosamine-1P, N-Acetylornithine, NAD+, NADH, NADP+, NADPH, Ornithine, Oxaloacetate, Phenylalanine, Phenylpyruvate, Phosphoenolpyruvate, Proline, Propionyl-CoA, PRPP, Pyruvate, Quinolinate, Riboflavin, Ribose-5-phosphate, Ribulose-5-phosphate, S-Adenosyl-L-methionine, Serine, Shikimic acid, Shikimate, Succinate, Succinyl-CoA, Threonine, Tryptophan, Tyrosine, UDP, UDP-glucose, UDP-glucuronate, UDP-N-acetylglucosamine, Uridine, UTP, Valine, and Xylulose-5-phosphate.

Figure 4:
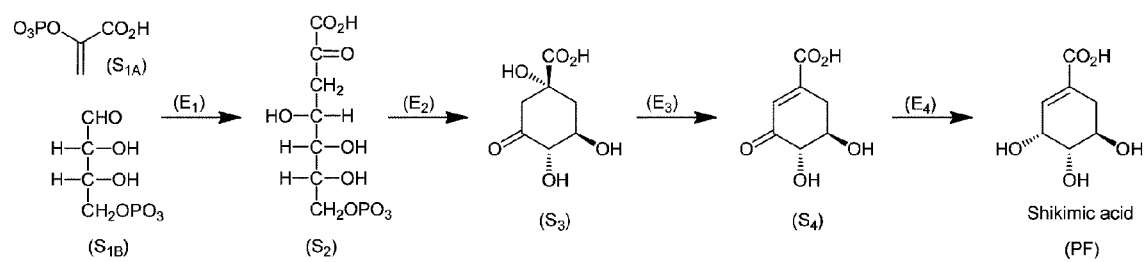
FIG. 4 depicts the pathway for the biosynthesis of shikimic acid.
Figure 5:
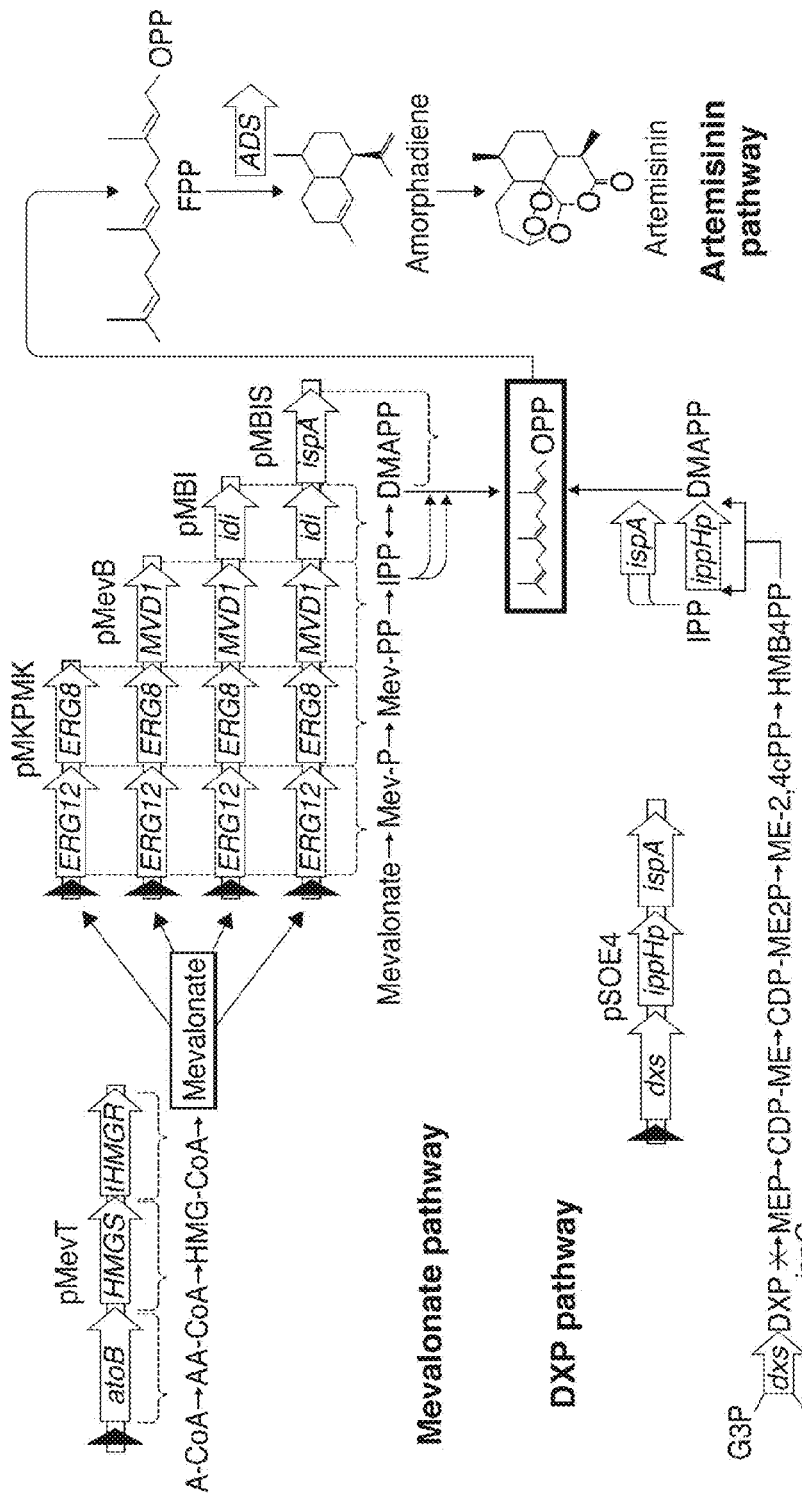
FIG. 5 depicts the pathway for biosynthesis of amorphadiene.

In certain embodiments, the pathway of interest provides for the synthesis of shikimic acid and/or shikimate (shikimate is the anionic form of shikimic acid) and synthetic intermediates thereto (e.g., as provided in FIG. 4), an isoprenoid or terpene (e.g., amorphadiene, farnesene, lycopene, astaxanthin, vitamin A, menthol, beta-carotene), poly-3-hydroxybutyrate, isobutanol, and 1-butanol (see, e.g., Examples 1-5 and FIGS. 4 and 5, provided herein).

A number of reactions may be catalyzed by enzymes in a pathway of interest. Broad classes of enzymes, which can be identified by enzyme classification number, provided in parentheses, include, but are not limited to:
  (EC 1) oxidoreductases; e.g., dehydrogenases, oxidases, reductases, oxidoreductases, synthases, oxygenases, monooxygenases, dioxygenases, lipoxygenases, hydrogenases, transhydrogenases, peroxidases, catalases, epoxidases, hydroxylases, demethylases, desaturases, dismutases, hydroxyltransferases, dehalogenases, and deiodinases;

(EC2) transferases; e.g., transaminases, kinases, dikinases, methyltransferases, hydroxymethyltransferases, formyltransferases, formiminotransferases, carboxytransferases, carbamoyltransferases, amidinotransferases, transaldolases, transketolases, acetyltransferases, acyltransferases palmitoyltransferases, succinyltransferases, malonyltransferases, galloyltransferases, sinapoyltransferases, tigloyltransferases, tetradecanoyltransferases, hydroxycinnamoyltransferases, feruloyltransferases, mycolyltransferases, benzoyltransferases, piperoyltransferases, trimethyltridecanoyltransferase, myristoyltransferases, coumaroyltransferases, thiolases, aminoacyltransferases, phosphorylases, hexosyltransferases, pentosyltransferases, sialyltransferases, pyridinylases, diphosphorylases, cyclotransferases, sulfurylases, adenosyltransferases, carboxyvinyltransferases, isopentenyltransferases, aminocarboxypropyltransferases, dimethylallyltransferases, farnesyltranstransferases, hexaprenyltranstransferases, decaprenylcistransferases, pentaprenyltranstransferases, nonaprenyltransferases, geranylgeranyltransferases, aminocarboxypropyltransferases, oximinotransferases, purinetransferases, phosphodismutases, phosphotransferases, nucleotidyltransferases, polymerases, cholinephosphotransferases, phosphorylmutases, sulfurtransferases, sulfotransferases, and CoA-transferases;

(EC3) hydrolases; e.g., lipases, esterases, amylases, peptidases, hydrolases, lactonases, deacylases, deacetylases, pheophorbidases, depolymerases, thiolesterases, phosphatases, diphosphatases, triphosphatases, nucleotidases, phytases, phosphodiesterases, phospholipases, sulfatases, cyclases, oligonucleotidases, ribonucleases, exonucleases, endonucleases, glycosidases, nucleosidases, glycosylases, aminopeptidases, dipeptidases, carboxypeptidases, metallocarboxypeptidases, omega-peptidases, serine endopeptidases, cystein endopeptidases, aspartic endopeptidases, metalloendopeptidases, threonine endopeptidases, aminases, amidases, desuccinylases, deformylases, acylases, deiminases, deaminases, dihydrolases, cyclohydrolases, nitrilases, ATPases, GTPases, halidases, dehalogenases, and sulfohydrolases;

(EC 4) lyases; e.g., decarboxylases, carboxylases, carboxykinases, aldolases, epoxylyases, oxoacid-lyases, carbon-carbon lyases, dehydratases, hydratases, synthases, endolyases, exolyases, ammonia-lyases, amidine-lyases, amine-lyases, carbon-sulfur lyases, carbon-halide lyases, phosphorus-oxygen lyases, and dehydrochlorinases;

(EC 5) isomerases; e.g., isomerases, racemases, mutases, tautomerases, phosphomutases, phosphoglucomutases, aminomutases, cycloisomerase, cyclases, topoisomerases; and (EC 6) ligases; e.g., synthetases, tNRA-ligases, acid-thiol ligases, amide synthases, peptide synthases, cycloligases, carboxylases, DNA-ligases, RNA-ligases, and cyclases.

More specific classes of enzymes include, without limitation, sub-classes of oxidoreductases, transferases, lyases, isomerases, and ligases, as provided below.

Exemplary oxidoreductases include, but are not limited to:
(EC 1.1) oxidoreductases acting on the CH—OH group of donors, and an acceptor;
(EC 1.2) oxidoreductases acting on the aldehyde or oxo group of donors, and an acceptor;
(EC 1.3) oxidoreductases acting on the CH—CH group of donors, and an acceptor;
(EC 1.4) oxidoreductases acting on the CH—NH2 group of donors, and an acceptor;
(EC 1.5) oxidoreductases acting on the CH—NH group of donors, and an acceptor;
(EC 1.6) oxidoreductases acting on NADH or NADPH, and an acceptor;
(EC 1.7) oxidoreductases acting on other nitrogenous compounds as donors, and an acceptor;
(EC 1.8) oxidoreductases acting on a sulfur group of donors, and an acceptor;
(EC 1.9) oxidoreductases acting on a heme group of donors, and an acceptor;
(EC 1.10) oxidoreductases acting on diphenols and related substances as donors, and an acceptor;
(EC 1.11) oxidoreductases acting on a peroxide as acceptor;
(EC 1.12) oxidoreductases acting on hydrogen as donor, and an acceptor;
(EC 1.13) oxidoreductases acting on single donors with incorporation of molecular oxygen, incorporating one or two oxygen atoms;
(EC 1.14) oxidoreductases acting on paired donors, with incorporation or reduction of molecular oxygen, with the donor being 2-oxoglutarate, NADH, NADPH, reduced flavin, flavoprotein, pteridine, iron-sulfur protein, ascorbate;
(EC 1.15) oxidoreductases acting on superoxide radicals as acceptor;
(EC 1.16) oxidoreductases oxidizing metal ions, and an acceptor;
(EC 1.17) oxidoreductases acting on CH or CH2 groups, and an acceptor;
(EC 1.18) oxidoreductases acting on iron-sulfur proteins as donors, and an acceptor;
(EC 1.19) oxidoreductases acting on reduced flavodoxin as donor, and an acceptor;
(EC 1.20) oxidoreductases acting on phosphorus or arsenic in donors, and an acceptor; and
(EC 1.21) oxidoreductases acting on X—H and Y—H to form an X—Y bond, and an acceptor; where acceptors for each donor category may include, without limitation: NAD, NADP, heme protein, oxygen, disulfide, quinone, an iron-sulfur protein, a flavin, a nitrogenous group, a cytochrome, dinitrogen, and H+.

Exemplary transferases include, but are not limited to:
(EC 2.1) transferases transferring one-carbon groups;
(EC 2.2) transferases transferring aldehyde or ketonic groups;
(EC 2.3) Acyltransferases;
(EC 2.4) Glycosyltransferases;
(EC 2.5) transferases transferring alkyl or aryl groups, other than methyl groups;
(EC 2.6) transferases transferring nitrogenous groups;
(EC 2.7) transferases transferring phosphorus-containing groups;
(EC 2.8) transferases transferring sulfur-containing groups; and
(EC 2.9) transferases transferring selenium-containing groups.

Exemplary hydrolases include, but are not limited to:
(EC 3.1) hydrolases acting on ester bonds;
(EC 3.2) Glycosylases;
(EC 3.3) hydrolases acting on ether bonds;
(EC 3.4) hydrolases acting on peptide bonds (peptidases);
(EC 3.5) hydrolases acting on carbon-nitrogen bonds, other than peptide bonds;
(EC 3.6) hydrolases acting on acid anhydrides;
(EC 3.7) hydrolases acting on carbon-carbon bonds;
(EC 3.8) hydrolases acting on halide bonds;
(EC 3.9) hydrolases acting on phosphorus-nitrogen bonds;

(EC 3.10) hydrolases acting on sulfur-nitrogen bonds;
(EC 3.11) hydrolases acting on carbon-phosphorus bonds;
(EC 3.12) hydrolases acting on sulfur-sulfur bonds; and
(EC 3.13) hydrolases acting on carbon-sulfur bonds.
Exemplary lyases include, but are not limited to:
(EC 4.1) Carbon-carbon lyases;
(EC 4.2) Carbon-oxygen lyases;
(EC 4.3) Carbon-nitrogen lyases;
(EC 4.4) Carbon-sulfur lyases;
(EC 4.5) Carbon-halide lyases; and
(EC 4.6) Phosphorus-oxygen lyases.
Exemplary isomerases include, but are not limited to:
(EC 5.1) Racemases and epimerases;
(EC 5.2) cis-trans-Isomerases;
(EC 5.3) Intramolecular isomerases;
(EC 5.4) Intramolecular transferases (mutases); and
(EC 5.5) Intramolecular lyases.
Exemplary ligases include, but are not limited to:
(EC 6.1) ligases forming carbon-oxygen bonds;
(EC 6.2) ligases forming carbon-sulfur bonds;
(EC 6.3) ligases forming carbon-nitrogen bonds;
(EC 6.4) ligases forming carbon-carbon bonds;
(EC 6.5) ligases forming phosphoric ester bonds; and
(EC 6.6) ligases forming nitrogen-metal bonds.

Isozymes (also known as isoenzymes) are enzymes that differ in amino acid sequence but catalyze the same chemical reaction. At some points in a pathway of interest, two or more isozymes may be present. Isozymes may display different kinetic parameters, or different regulatory properties.

Enzymes involved in a pathway of interest or associated pathway may also be classified according to the role of the enzyme. Direct involvement enzymes (class 1) in a cell or cell lysate catalyze a reaction in the pathway. It is typical of pathways that such direct enzymes are one of a chain, where a product of a first enzyme is the substrate of a second enzyme, the product of the second enzyme is the substrate of a third enzyme, and so forth, which eventually results in the product of interest. Indirect involvement enzymes (class 2) in a cell or cell lysate react in an associated pathway, usually in the production of a substrate used in the pathway of interest. It may be a characteristic of an enzyme in these two classes that overproduction ("overexpression") of the enzyme is toxic to the cell, even 2-fold, 3-fold, or more overproduction. Such toxicity can be the result of overproduction of a product that is toxic at high concentrations, or that the enzyme diverts resources at a rate that impacts normal cell physiology. The expression of such enzymes benefits from modulated selective accumulation in a separate compartment with the methods of the invention, such as through the use of an inducible promoter, in order to avoid undesirable stress on the cell.

Within a pathway, enzymes will vary in turnover rate and the effectiveness with which a product is produced. As a result, certain enzymes in a pathway become rate-limiting. Increasing the concentration of rate-limiting enzymes in a pathway (relative to non-rate limiting enzymes) allows increased flux through the pathway of interest (see, e.g., Zamboni et al. *Nature Protocols* (2009) 4:878-892, incorporated herein by reference). Often rate-limiting enzymes are associated with toxicity when over-produced, and thus the available concentrations of such enzymes is desirably modulated by the methods of the invention to selectively increase accumulation of the rate limiting activity at a selected time point and possibly also while being sequestered to a separate compartment.

A third class of enzymes in a cell or cell lysate are competing enzymes (class 3), which utilize a substrate or product of the pathway of interest. A characteristic of a competing enzyme is that the kinetics of the substrate conversion are sufficiently high that the presence of the enzyme decreases the overall yield and/or the rate of production of the desired final product catalyzed by the pathway of interest. A normal cell may require the expression of competing enzymes, and therefore rather than knocking out expression of competing enzymes completely, it is desirable to selectively decrease the concentration of the enzyme; see, e.g., PCT Publication No. WO 2010/077806, incorporated herein by reference.

For convenience of naming, an enzyme in the pathway may be categorized as a first, pathway entry enzyme, or a subsequent downstream enzyme or enzymes. For convenience, the pathway entry enzyme may be referred to herein as $E_1$, and the downstream enzymes may be consecutively numbered, $E_2, E_3, \ldots E_n$. Pathways of interest for use in the methods of the present invention will usually comprise at least one enzyme, at least two enzymes, at least three enzymes, at least four enzymes, or more, e.g., between 1 to 50 enzymes, between 1 to 40 enzymes, between 1 to 30 enzymes, between 1 to 20 enzymes, between 1 to 10 enzymes, between 1 to 5 enzymes, between 1 to 2 enzymes, between 2 to 50 enzymes, between 2 to 40 enzymes, between 2 to 30 enzymes, between 2 to 20 enzymes, between 2 to 10 enzymes, between 2 to 5 enzymes, between 2 to 4 enzymes, between 5 to 50 enzymes, between 5 to 40 enzymes, between 5 to 30 enzymes, between 5 to 20 enzymes, between 5 to 10 enzymes, between 5 to 8 enzymes, between 10 to 50 enzymes, between 10 to 40 enzymes, between 10 to 30 enzymes, or between 10 to 20 enzymes, inclusive.

Enzymes in a pathway may be naturally occurring, or modified to optimize a particular characteristic of interest, e.g. substrate specificity, reaction kinetics, solubility, and/or insensitivity to feedback inhibition. In addition, in some cases, the gene expressing the enzyme will be optimized for codon usage within the host cell. In some embodiments, the complete pathway comprises enzymes from a single organism, however such is not required, and combining enzymes from multiple organisms is also contemplated. For some purposes, a pathway may be endogenous to the host cell, but such is also not required, and a complete pathway or components of a pathway may be introduced into a host cell. Where the system is provided in an intact cell, generally the complete set of enzymes of the pathway of interest will be present in the cell. For purposes of cell-free production, one or more enzymes may be added to the lysate, or alternatively may be produced by the lysate, so as to complete the pathway.

In the pathway system, a first substrate ($S_1$) is acted upon by the pathway entry enzyme, and is converted to a first product, although it will be understood by one of skill in the art that an enzyme may act upon more than one substrate simultaneously, and may produce more than one product, such that two or more pathways may be interconnected at a single enzyme. The first product is a substrate ($S_2$) for downstream enzyme $E_2$, and is converted to a second product by $E_2$. Depending on the complexity of the pathway, the second product may be the final product (PF), or may be a substrate ($S_3$) for a third downstream enzyme ($E_3$), and is converted to a third product by $E_3$, which may be a substrate ($S_4$) for a fourth enzyme. The final enzyme in the pathway, which may be $E_2$, $E_3$, $E_4$, etc. produces the product of interest (PF). It is a characteristic of enzymatic pathways that the product of one enzyme is the substrate for the next enzyme. Products may be stable or relatively labile, but in general the final product is sufficiently stable that it can be isolated from the cell, cell lysate, or reaction mixture. Competing enzymes utilize a substrate or product of the pathway of interest, which may include any one of PF, $S_1$, $S_2$, $S_3$, and/or $S_4$, and may be referred to as competing enzymes ($E_c$).

In some embodiments of the invention, the initial substrate, $S_1$, is a central metabolite, or cellular "commodity". The central pathways of metabolism include glycolysis and the citric acid cycle. Such $S_1$ compounds are generally not specific to the pathway of interest, but are compounds widely found in various cells and are substrates for multiple enzymes and pathways. Examples of commodity substrates include, without limitation, glucose, ATP, pyruvate, phosphoenol pyruvate, and the like. A pathway entry enzyme, $E_1$, may convert a commodity substrate to a product that is a selective substrate for one or a relatively small number of enzymes.

In general, a key entry enzyme is defined as one that performs the first committed step in a pathway to a product of interest. This step generally involves the biochemical commitment of a compound to the pathway of a product of interest. Examples of key entry enzymes include, but are not limited to, those set forth in Table 2.

normal levels; and where at least one key enzyme of the pathway is (a) expressed at high levels and (b) relocated to a compartment other than the naturally occurring compartment. In some embodiments the key enzyme is sequestered in the periplasm. The key enzyme controls flux through the pathway of interest, and may be a pathway entry enzyme and/or a rate-limiting enzyme. A native counterpart to the key enzyme(s) is usually expressed at normal levels in the cytoplasm. During cell culture it may be desirable to control the components of the growth medium of the cells in order to avoid exposure of the periplasmic sequestered enzyme to conditions that may decrease its activity, e.g. exposure to metals and the like. For example, it has been found that DAHP synthase in the shikimic acid pathway can be inactivated through copper-catalyzed oxidation, and thus it is desirable to modify the culture conditions by increasing the concentration of manganese and magnesium metals in the growth medium

TABLE 2

Exemplary list of key pathway entry enzymes

| Key Entry Enzyme(s) | Biosynthetic Pathway | Example Products | E. coli enzyme |
|---|---|---|---|
| amidophosphoribosyl transferase | purine biosynthesis | GMP, GDP, GTP, dGDP, dGTP, AMP, ADP, ATP, dADP, dATP, inosine monophosphate | PurF |
| orotate phosphoribosyltransferase | pyrimidine biosynthesis | UMP, UDP, UTP, CDP, CTP | PyrE |
| 2-dehydro-3-deoxyphosphoheptonate aldolase | chorismate biosynthesis | Shikimate, Tyrosine, Phenylalanine, Tryptophan | AroE, F, G |
| phosphoribosyltransferase HisG | histidine biosynthesis | Histidine | HisG |
| acetolactate/acetohydroxybutanoate synthase | isoleucine, leucine, valine biosynthesis | Isoleucine, Leucine, Valine | IlvH, M, N |
| UDP-N-acetylglucosamine acyltransferase | lipopolysaccharide biosynthesis | Lipid A disaccharide | LpxA |
| aspartate aminotransferase | lysine, threonine and methionine biosynthesis | Lysine, Threonine, Methionine | AspC |
| arginine decarboxylase | putrescine biosynthesis | Putrescine | SpeA |
| GTP cyclohydrolase I | tetrahydrofolate biosynthesis | Tetrahydrofolate | FolE |
| acetyl-CoA carboxylase | fatty acid biosynthesis | Malonyl-CoA | AccA, B, C, D |

A specific non-limiting example of a pathway, provided for illustrative purposes, is the pathway for the synthesis of shikimic acid (see FIG. 4). In this pathway, for example, a reaction between the cellular commodity compounds phosphoenolpyruvate ($S_{1A}$) and erythrose-4-phosphate ($S_{1B}$) is catalyzed by the enzyme DAHP synthase ($E_1$) to form 3-deoxy-D-arabinoseheptulose-7-phosphate (DAHP). DAHP ($S_2$) is transformed to 3-dehydroquinate (3-DHQ) by the second enzyme in the pathway, DHQ synthase ($E_2$). 3-DHQ ($S_3$) is dehydrated to 3-dehydroshikimate by the third enzyme in the pathway, 3-DHQ dehydratase ($E_3$). 3-dehydroshikimate ($S_4$) is reduced to shikimic acid (PF) by the fourth enzyme in the pathway, shikimate dehydrogenase ($E_4$), using NADPH as a cofactor. The enzymes of the pathway are known in the art and have been characterized in a number of organisms, including, for example, E. coli, in which the enzymes are encoded by the genetic loci as follows: DAHP synthase (aroG, aroF, aroH); DHQ synthase (aroB); 3-DHQ dehydratase (aroD); shikimate dehydrogenase (aroE); see, e.g., PCT Publication No. WO2010/074760, incorporated herein by reference.

Production Methods

High yield production of a product of interest is accomplished by providing a cell in which cytoplasmic enzymes comprising a pathway of interest are expressed, e.g. at physiologically normal levels, or at greater than physiologically to outcompete available copper (see, e.g., Bauerle et al., J. Bacteriol. (1999) 181:1636-1642; and Stadtman et al., J. Biol. Chem. (1991) 266:2005-2008, each incorporated herein by reference). In other embodiments, cofactor(s) are provided or concentrations of co-factor(s) are altered in the growth medium to enhance enzyme activation in the periplasm or other relocated enzyme site.

For production purposes, a lysate of the cell is utilized, wherein the periplasmically sequestered enzyme is brought into operable contact with the enzymes of the pathway of interest expressed in the cytoplasm. Cells are lysed by any convenient method that substantially maintains enzyme activity, e.g. sonication, French press, and the like as known in the art. The lysate may be fractionated, particulate matter spun out, or may be used in the absence of additional processing steps. The cell lysate may be further combined with one or more substrates, enzymes, nutrients, co-factors, buffers, reducing agents, and/or ATP generating systems, etc., as required for enzyme activity. Such a system, in certain embodiments, may be referred to herein as a "cell-free system," i.e., an isolated system containing a cell lysate or extract expressly engineered to synthesize an enzyme or cascade of enzymes that, when acting in a given sequence (e.g., in an enzymatic pathway) and proportion over a determined substrate, results in the preferential generation of a product, the compound of interest. A compound of interest is typically a chemical entity (e.g., a small organic molecule), which can be used as an active pharmaceutical ingredient (API), chemical precursor, or intermediate.

As used herein, a "substrate" is a compound or mixture of compounds capable of providing the required elements needed to synthesize a compound of interest.

As used herein, a "small organic molecule" or "small molecule" refers to an organic molecule with a molecular weight of less than 800 g/mol (e.g., less than 700 g/mol, less than 600 g/mol, less than 500 g/mol, less than 400 g/mol, less than 300 g/mol, less than 200 g/mol, less than 100 g/mol, between 50 to 800 g/mol, inclusive, between 100 to 800 g/mol, inclusive, or between 100 to 500 g/mol, inclusive). In certain embodiments, the small organic molecule is a therapeutically active agent such as a drug (e.g., a small organic molecule approved by the U.S. Food and Drug Administration as provided in the Code of Federal Regulations (CFR)). The small organic molecule may also comprise a metal. In this instance, the small organic molecule is also referred to as an "small organometallic molecule."

As used herein, a "reducing equivalent" or "reducing agent" is a chemical species which transfers the equivalent of one electron in a redox reaction. Examples of reducing equivalents are a lone electron (for example in reactions involving metal ions), a hydrogen atom (consisting of a proton and an electron), and a hydride ion (:H—) which carries two electrons (for example in reactions involving NAD). A "reducing equivalent acceptor" is a chemical species that accepts the equivalent of one electron in a redox reaction.

As used herein, an "adenosine triphosphate regeneration system" or "ATP regeneration system" is a chemical or biochemical system that converts adenosine, AMP, and ADP into ATP. Examples of ATP regeneration systems include those involving glucose metabolism, glutamate metabolism, and photosynthesis.

Lysates of cells of different genetic backgrounds (e.g. previously altered or genetically engineered) or species, or that are prepared by different strategies can be mixed and simultaneously or sequentially used in a bioprocess with the cell lysate of the invention. The lysate can be free or immobilized, and can be reused or disposed at each stage of the process. For example, in certain embodiments, the cell lysate is a lysate of an *E. coli* organism engineered to overexpress one or more enzymes in the pathway of interest. In certain embodiments, the cell lysate is a combination of different cell lysates, e.g., a combination of two, three, four, five, six, seven, eight, nine, or ten different cell lysates, obtained from two, three, four, five, six, seven, eight, nine, or ten different *E. coli* organisms each engineered to overexpress one or more enzymes in the pathway of interest.

The methods of the invention provide for high yields of the desired product, which yield is greater than the yield that can be achieved with a native microbial host. Productivity (i.e. rate of production per unit of volume or biomass) may also be increased. In one embodiment of the invention, the yield of product is at least about 2-fold above the basal rate, at least about 5-fold above the basal rate, at least about 10-fold above the basal rate, at least about 25-fold above the basal rate, at least about 50-fold above the basal rate, or more, e.g., between about 2-fold to about 100-fold above the basal rate. In certain embodiments, the rate of yield of the product using the inventive methods is between about 0.1 to 20 grams of product/L/h.

Different inocula can be adapted to different conditions (e.g. two batches grown on two different carbon sources) or can have different genotypes and then mixed to carry out the process (e.g. to get simultaneous consumption of a mix of carbon sources or sequential processing of a metabolite through a pathway divided in two separate batches of cells). A process can also take place sequentially by allowing one set of reactions to proceed in one vessel and then transferring the supernatant to a second vessel.

The reactions may utilize a large scale reactor, small scale, or may be multiplexed to perform a plurality of simultaneous syntheses. Continuous reactions will use a feed mechanism to introduce a flow of reagents, and may isolate the end-product as part of the process. Batch systems are also of interest, where additional reagents may be introduced over time to prolong the period of time for active synthesis. A reactor may be run in any mode such as batch, extended batch, semi-batch, semi-continuous, fed-batch, and continuous, and which will be selected in accordance with the application purpose.

The reactions may be of any volume, either in a small scale (e.g., usually at least about 1 ml and not more than about 15 ml) or in a scaled up reaction (e.g., where the reaction volume is at least about 15 ml, usually at least about 50 ml, more usually at least about 100 ml, and may be 500 ml, 1000 ml, or greater up to many thousands of liters of volume). Reactions may be conducted at any scale.

Various salts and buffers may be included, where ionic species are typically optimized with regard to product production. When changing the concentration of a particular component of the reaction medium another component may be changed accordingly. Also, the concentration levels of components in the reactor may be varied over time. The adjuster of the thiol/disulfide oxidation/reduction potential may be dithiothreitol, ascorbic acid, glutathione and/or their oxidized forms. Other adjusters of the general redox potential may also be used.

In a semi-continuous operation mode, the reactor may be operated in dialysis, diafiltration batch or fed-batch mode. A feed solution may be supplied to the reactor through the same membrane or a separate injection unit. Synthesized product is accumulated in the reactor, and then is isolated and purified according to the usual method for purification after completion of the system operation. Alternatively, product can be removed during the process either in a continuous or discontinuous mode with the option of returning part or all of the remaining compounds to the reactor.

Where there is a flow of reagents, the direction of liquid flow can be perpendicular and/or tangential to a membrane. Tangential flow is effective for recycling ATP and for preventing membrane plugging and may be superimposed on perpendicular flow. Flow perpendicular to the membrane may be caused or effected by a positive pressure pump or a vacuum suction pump or by applying transmembrane pressure using other methods known in the art. The solution in contact with the outside surface of the membrane may be cyclically changed, and may be in a steady tangential flow with respect to the membrane. The reactor may be stirred internally or externally.

The amount of product produced in a reaction can be measured in various ways, for example, by enzymatic assays which produce a colored or fluorometric product or by HPLC methods. In certain embodiments, the product is measured utilizing an assay which measures the activity or concentration of the particular product being produced.

EXAMPLES

The following examples are put forth so as to provide those of ordinary skill in the art with a complete disclosure and description of how to make and use the present invention, and are not intended to limit the scope of the invention or to represent that the experiments below are all or the only experiments performed. Efforts have been made to ensure accuracy with respect to numbers used (e.g., amounts, temperature, and the like), but some experimental errors and deviations may be present. Unless indicated otherwise, parts are parts by weight, molecular weight is weight average molecular weight, temperature is in degrees Celsius, and pressure is at or near atmospheric pressure.

Example 1

Production of Shikimic Acid

Shikimic acid is an intermediate in the chorismate biosynthetic pathway, where the key entry enzyme is 2-dehydro-3-deoxyphosphoheptonate aldolase (3-deoxy-D-arabinoheptulosonate-7-phosphate, DAHP, synthase). DAHP synthase catalyzes the first committed step in shikimate production by converting the central metabolites phosphoenolpyruvate (PEP) and erythrose-4-phosphate (E4P) to DAHP. In E. coli, there are three DAHP synthase enzymes—AroG, AroE, and AroF—encoded by genes aroG, aroE, and aroF, respectively. It is common that feedback resistant versions of these enzymes (Kikuchi et al., Appl. Environ. Microbiol. (1997) 63:761; Ray et al., J. Bacteriol. (1988) 170:5500; Weaver and Herrmann, J. Bacteriol. (1990) 172:6581) are used to ensure maximal activity.

In this example, a DAHP synthase gene is modified to contain various periplasmic signal sequences (periplasmic leader peptides) targeting the enzyme to the periplasm. Expression optimization, evaluation of various DAHP synthases, and periplasmic protease site identification and removal are used to address potential risks and challenges associated with targeted periplasmic expression. Expression of active DAHP synthase in the periplasm is verified, and coupled with cyoplasmic over-expression of downstream pathway genes to demonstrate more robust growth of the engineered strain post-induction (relative to a strain over-expressing select pathway genes in the cytoplasm only), followed by demonstration of increased flux to the product of interest post-lysis in an active, cell-free reaction.

AroG is targeted for expression in the periplasm of E. coli. DNA sequences coding for various periplasmic leader peptides are added to the aroG gene through PCR amplification to create a library of DNA sequences coding for AroG with different periplasmic leader peptides on the N-terminus of the protein (PerS-AroG library). Alternatively, DNA sequences coding for the PerS-AroG library are created by DNA synthesis. Several periplasmic signal sequences are tested to determine which is most efficient in producing the highest level of active enzyme in the periplasm. Suitable periplasmic leaders are set forth in Tables 4 and 5 of Example 2. The DNA sequences coding for the PerS-AroG library are inserted in suitable expression vectors to create a library of PerS-AroG expression vectors. The library of expression vectors is used to transform a suitable strain of E. coli that is plated out and screened for PerS-AroG expression and periplasmic localization of AroG. The selected construct can be further optimized for expression by testing a plurality of promoters and ribosome binding sites.

For example, DNA sequences coding for the PerS-AroG library is cloned in a pDuet vector for inducible expression from the T7lacO promoter. E. coli strain BL21(DE3), or similar strain expressing the T7 polymerase, is transformed with the PerS-AroG library-containing plasmids. Expression modification is achieved through use of varying levels of the inducer isopropyl-β-D-1-thiogalactopyranoside (IPTG), through use of variant promoters and ribosome binding sites, as well as through use of copy number variation among different pDuet vectors. Other plasmids, expression systems, or strains familiar to those skilled in the art may also be used.

Several strains are created with pDuet-expressed versions of AroG both with various periplasmic leaders, and without a periplasmic leader. Culture is grown to intermediate optical density in rich defined media prior to expression induction with 0.05-1 mM IPTG. Expression is induced for several hours to enable buildup of DAHP synthase in the periplasm. Periplasmically-targeted DAHP synthase is extracted using osmotic shock, or other methods known to those skilled in the art. Verification of expression of full-length protein is determined by denaturing protein gel electrophoresis with appropriate standards. Various methods may be used to optimize expression or folding of the periplasmically-targeted DAHP synthase (or other enzymes). These include, but are not limited to, the following: i) optimizing expression through use of varying IPTG levels, differing plasmid origins of replication, and/or modification of RBS and/or promoters, ii) identifying and removing known sites for specific periplasmic proteases through conservative amino acid substitutions, and iii) use of orthologous enzymes. Data indicate periplasmic expression of full-length AroG when OmpA and STII periplasmic signal sequences are used, as shown in FIG. 1.

The specific activity of periplasmically-targeted DAHP synthase is determined in whole cell or periplasmic extract using a continuous spectrophotometric assay monitoring absorbance at 232 nm to measure conversion of PEP (with E4P) to DAHP. For example, the whole cell or periplasmic extract contains 10 mM Tris-HCl (pH 7.5) with 35 mM potassium phosphate (pH 7.0) and 500 uM PEP-K to stabilize the protein. Prior to assay, the extract is passed through a Sephadex G-25 column equilibrated with the same buffer solution to remove amino acids and other molecules less than 5 kDa. One microliter of purified extract is added to 99 microliters reaction mix (100 uM PEP-K, 300 uM E4P-Na, 10 mM 1,3-bis[tris(hydroxymethyl)methylamino]propane, 10 uM $MgCl_2$, pH 7.0) and absorbance at 232 nm is monitored over the course of 0.5-2 hours. Appropriate control extracts from strains not over-expressing AroG, as well as control reactions performed without E4P, are included for normalization. The concentration of total protein in the whole cell or periplasmic extract is determined using a standard Bradford assay familiar to those skilled in the art. The fraction of whole cell or periplamic protein that is AroG is determined through analysis of images of coomassie-stained polyacrylamide gels of whole cell or periplasmic extract.

Because it is known that $Cu^{++}$ causes the irreversible inactivation of DAHP synthase (Park and Bauerle, J. Bacteriol. (1999) 181:1636) measures such as limiting the $Cu^{++}$ content of the growth medium and increasing the concentrations of other divalent cations such as $Mn^{++}$ can be used to encourage full activation of the enzyme as well as to preserve its activity. Upon demonstration of activity of a periplasmically-expressed AroG, additional enzymes in the biochemical pathway to shikimic acid useful for providing pathway precursors or other pathway substrates (listed below) are subcloned in pDuet vectors for cytoplasmic overexpression in E. coli BL21 (DE3) as described above.

TABLE 3

| EC# | Enzyme | E. coli | Genbank Accession No. |
|---|---|---|---|
| 2.2.1.1 | transketolase | TktA | AAT48155.1 |
| 4.2.3.4 | dehydroquinate synthase | AroB | AAC76414.1 |

TABLE 3-continued

| EC# | Enzyme | E. coli | Genbank Accession No. |
|---|---|---|---|
| 4.2.1.10 | dehydroquinate dehydratase | AroD | AAC74763.1 |
| 1.1.1.25 | shikimate dehydrogenase | AroE | AAC76306.1 |

Overexpression of one or several of these enzymes has been shown to improve shikimic acid production in vivo (Patnaik and Liao, *Appl. Environ. Microbiol.* (1994) 60:3903; Flores et al., *Nat. Biotechnol.* (1996) 14:620; Herrmann, *Plant Physiol.* (1995) 107:7; Bongaerts et al., *Met. Eng.* (2001) 3:289; Kramer et al., *Met. Eng.* (2003) 5:277). In the case of transketolase (TktA), an enzyme with the purpose of increasing the supply of a pathway precursor (erythrose 4-phosphate), the enzyme will be exported to the periplasm if transketolase overexpression is observed to be detrimental to the growth of the organism. In a similar example, the soluble nucleotide transhydrogenase (SthA gene product) may also be evaluated for overexpression either in the cytoplasm or the periplasm to assess the effect of its cytoplasmic overexpression on growth. Additionally, a vector containing a cytoplasmically-targeted DAHP synthase is included to serve as a cell growth control. Each pDuet vector can express two genes from individual promoters, ensuring maximal expression of all proteins with up to three vectors. Polycistronic arrangement of genes can be used to express all genes from a single vector if this is necessary for improved cell growth.

Denaturing protein gel electrophoresis with appropriate standards is performed to ensure expression of full-length protein in the cytoplasm. Upon confirmation of full-length protein expression, plasmids are cotransformed into BL21 (DE3) and co-transformants are selected on appropriate antibiotic media to ensure presence of all plasmids. As described above, cells are grown in rich defined media to intermediate optical density, and overexpression is induced by addition of 0.05-1 mM IPTG. Spectrophotometric measurement of culture optical density at defined intervals is used to determine generation time for cells overexpressing TktA, AroB, AroD, and AroE in the cytoplasm together with DAHP synthase overexpressed in either the cytoplasm (control) or periplasm.

At various time points post-induction, cells are harvested, lysed through use of a high-pressure homogenizer, and mixed with glucose, glutamate and other substrates to be used in a cell-free reaction for the production of shikimate. Levels of shikimate (and intermediates including 3-dehydroquinate and 3-dehydroshikimate) are measured via HPLC using methods familiar to those skilled in the art. The rate and extent of growth as well as the levels and production rate of shikimate in the lysate are compared when DAHP synthase is expressed in the periplasm relative to those obtained when DAHP synthase is expressed in the cytoplasm.

Example 2

Growth Effects and Activity of Periplasmically-Expressed AroG

Periplasmic expression of DAHP synthase. A library of plasmids is constructed containing the gene coding for AroG (Genbank Acc. no. AAC73841.1) modified with various periplasmic signal sequences targeting the enzyme to the periplasm. The DNA sequences of primers used to construct the coding sequences for the periplasmic leaders tested are set forth in Tables 4 and 5. DNA sequences coding for a set of periplasmic signal sequences are added to the aroG gene through PCR amplification using the following primers:

TABLE 4

Primers Used to Add Periplasmic Targeting Signals to aroG

| Leader | Primer | Sequence |
|---|---|---|
| none | F 5' | gcaattcggtctcccatgaattatcagaacgacgatttacgcatc (SEQ ID NO: 11) |
|  | R 3' | gaattcgcggccgcttacccgcgacgcgcttttac (SEQ ID NO: 12) |
| OmpA | F 5' | gcaattcggtctcccatgaaaaaaacggcaattgcgatagcg (SEQ ID NO: 13) |
|  | R 3' | gaattcgcggccgcttacccgcgacgcgcttttac (SEQ ID NO: 14) |
| StII | F 5' | gcaattcggtctcccatgaaaaaaaatattgctttcctgctcg (SEQ ID NO: 15) |
|  | R 3' | gaattcgcggccgcttacccgcgacgcgcttttac (SEQ ID NO: 16) |
| DsbA | F 5' | gcaattcggtctcccatgaaaaagatttggctggcgctg (SEQ ID NO: 17) |
|  | R 3' | gaattcgcggccgcttacccgcgacgcgcttttac (SEQ ID NO: 18) |
| MalE | F 5' | gcaattcggtctcccatgaaaataaaaacaggtgcacgcatcc (SEQ ID NO: 19) |
|  | R 3' | gaattcgcggccgcttacccgcgacgcgcttttac (SEQ ID NO: 20) |
| PhoA | F 5' | gcaattcggtctcccatgaaacaaagcactattgcactggc (SEQ ID NO: 21) |

TABLE 4-continued

Primers Used to Add Periplasmic Targeting Signals to aroG

Leader Primer Sequence

| | | | |
|---|---|---|---|
| | R 3' | gaattcgcggccgcttacccgcgacgcgcttttac (SEQ ID NO: 22) | |
| SfmC | F 5' | gcaattcggtctcccatgatgactaaaataaagttattgatgctc (SEQ ID NO: 23) | |
| | R 3' | gaattcgcggccgcttacccgcgacgcgcttttac (SEQ ID NO: 24) | |

TABLE 5

Reverse primer for addition of C-term 6xHis tag to all constructs

Primer Sequence

| | |
|---|---|
| R 3' | GAATGCGGCCGCTTAGTGGTGATGATGGTGATGCCCGCGACGCGCTTTTAC (SEQ ID NO: 25) | aroG constructs PCR-amplified using the primers in Tables 4 and 5 are digested with BsaI/NotI and subcloned in a NcoI-NotI digested pDuet vector for inducible expression. *E. coli* strain BL21(DE3) is transformed with plasmids containing the subcloned, periplasmically-targeted AroG. Expression modification is achieved through use of varying levels of IPTG as well as through use of copy number variation among different pDuet vectors. Other plasmids, expression systems, or strains familiar to those skilled in the art may also be used.

Frozen working stock cell cultures of the following strains:
a. BL21(DE3):pACYC-Duet1 (empty vector control)
b. BL21(DE3):pACYC-AroG (without periplasmic signal sequence)
c. BL21(DE3):pACYC-OmpA-AroG (containing AroG with OmpA periplasmic signal sequence)
d. BL21(DE3):pACYC-STII-AroG (containing AroG with STII periplasmic signal sequence)

were inoculated to an optical density at 600 nm of 0.0025 in 250 ml of EZ Rich defined medium (Neidhardt et al. *J. Bacteriol.* (1974) 119:736) containing 34 μg/mL chloramphenicol. After growth at 37° C. to OD600 0.6, 0.1 mM IPTG was added to induce protein expression. Growth and induction were then carried out for 16 h at 25° C.

Whole cell, periplasmic, and cytoplasmic fractions were obtained using methods familiar to those skilled in the art (e.g., see Chen et al., *Biochem. Eng. J.* (2004) 19:211; Soares et al., *Prot. Eng.* (2003) 16:1131). Specifically, whole cell fractions were obtained by harvesting 12 ml culture at 3000×g for 30 min at 4° C. Cell pellets were re-suspended in 12 ml of 1 mM Tris-HCl, pH 7.0. Resuspended cells were lysed in two passes through an EmulsiFlex-C3 high pressure homogenizer (Avestin, Canada) at 15000-17000 psi. To remove cell debris, samples were centrifuged at 21000×g for 15 min. Periplasmic and cytoplasmic fractions were obtained as follows: 200 ml culture was harvested at 3000×g for 30 min at 4° C. Cell pellets were gently resuspended in 2 ml of 4° C. 1 mM Tris HCl pH 7.0, then centrifuged at 3000×g for 30 min. The supernatant was used as the periplasmic fraction and the pellet was further processed to obtain the cytoplasmic fraction. Vigorous resuspension of the pellet in 11 ml of 50 mM Tris-HCl and 50 mM NaCl, followed by lysis and clarification as described for the whole cell extract, yielded the cytoplasmic fraction.

Verification of expression of full-length protein is determined by denaturing protein gel electrophoresis with appropriate standards. Specifically, 19.5 uL of SDS-PAGE running buffer containing 0.04 M dithiothreitol (DTT) is added to 39 ul extract, then incubated 5 min at 99° C. Samples were run on 10% Bis-Tris gels at 200 V for 55 minutes. Western blots were performed by transferring proteins on a nitrocellulose membrane using XCell II™ Blot Module at 30 V for 90 minutes. Membranes were then washed twice with PBS (phosphate buffered saline) for 5 min followed by 1 h block step with PBS and 1% non-fat dry milk (room temperature on an orbital shaker). A C-terminal anti-His HRP (horse radish peroxidase) antibody (Invitrogen) was diluted 1:5000 in blocking buffer and incubated with the washed membrane for 1 h. Proteins containing a His-Tag on the C-terminal end were observed on the nitrocellulose membrane after incubation in TMB immune-blot solution (Invitrogen). Data indicate periplasmic expression of full-length AroG when OmpA and STII periplasmic signal sequences are used, as shown in FIG. 1.

Activity of Periplasmically-Expressed DAHP Synthase.

Figure 2:
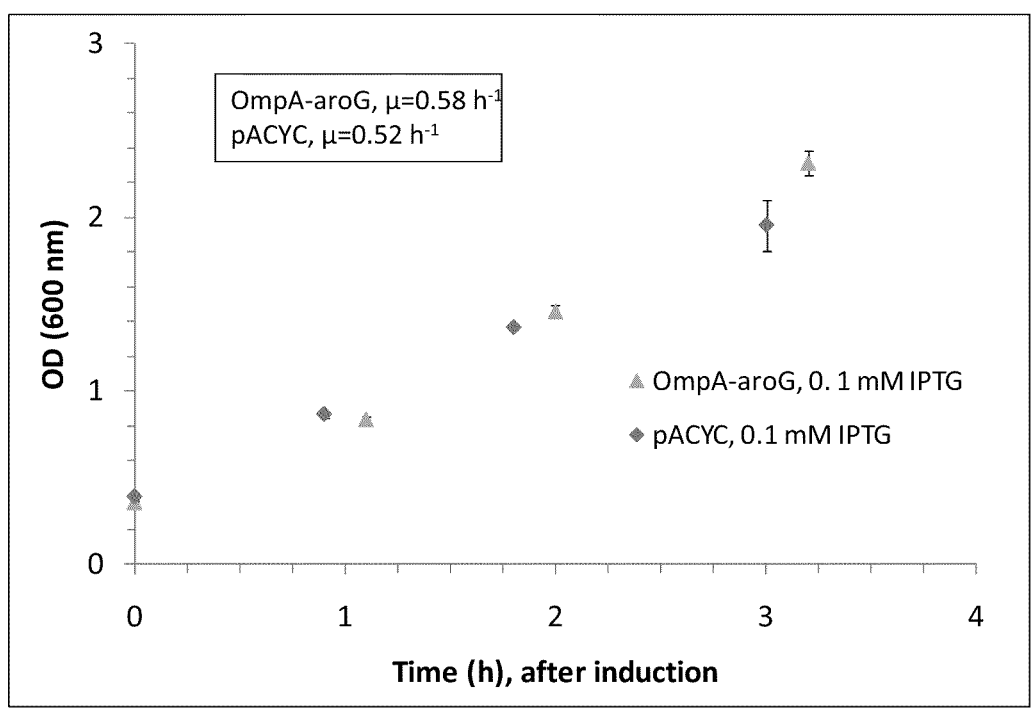
FIG. 2 depicts growth data from cell cultures of BL21 (DE3) expressing OmpA-aroG or a pACYC empty vector control, indicating that periplasmic expression of AroG has no negative effect on cell growth.

Cultures of BL21(DE3) expressing OmpA-aroG, or containing a pACYC empty vector control were grown in 50 ml EZ-Rich defined medium supplemented with 50 uM MnCl$_2$ at 37° C. Cultures were induced with 0.1 mM IPTG when OD600 reached 0.3 and grown an additional 3 h at 30° C. Cultures were harvested by centrifugation at 3000×g for 20 min followed by resuspension in 13 ml of 35 mM potassium phosphate buffer, pH 7, and 0.5 mM PEP. Cells were lysed by homogenization at 15000 psi. FIG. 2 contains growth data from these strains, indicating that periplasmic expression of AroG has no negative effect on cell growth.

Figure 3:
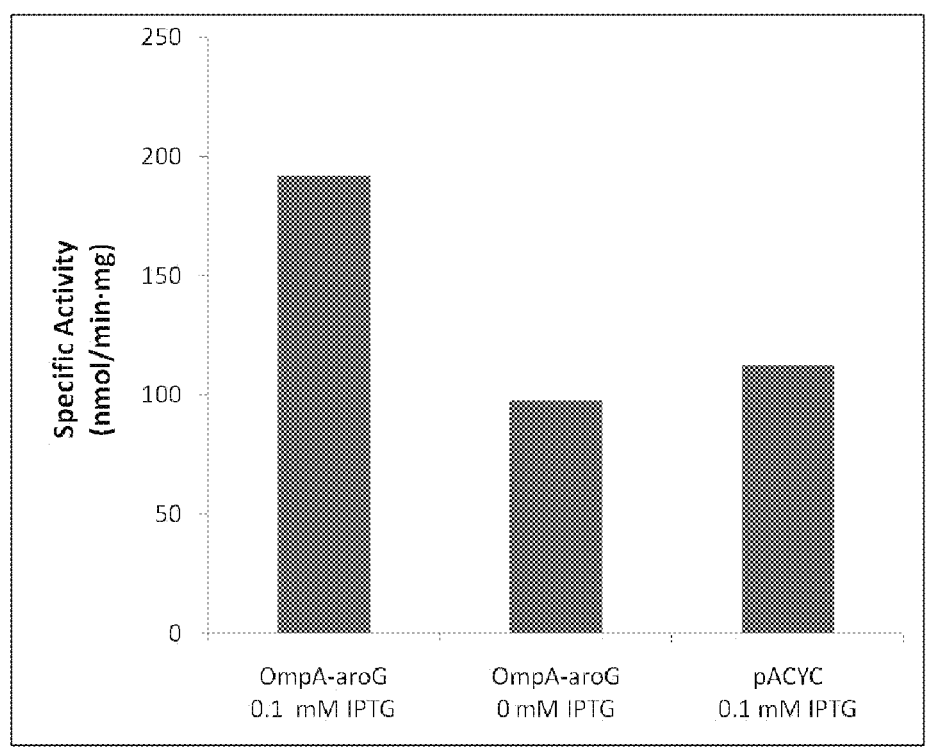
FIG. 3 shows the specific activity of periplasmically-expressed 3-deoxy-D-arabinoheptulosonate-7-phosphate (DAHP) synthase.

The specific activity of periplasmically-targeted DAHP synthase is determined using a continuous spectrophotometric assay monitoring absorbance at 232 nm to measure conversion of PEP (with E4P) to DAHP. DAHP synthase activity assays were performed on whole cell extract protein fractions of BL21(DE3) strains expressing OmpA-aroG, or containing a pACYC empty vector control. Protein fractions were purified by gel filtration using PD SpinTrap G-25 columns (GE Healthcare). Reaction mixtures contained 100 μM PEP, 300 μM E4P, 10 mM bis-tris propane buffer (pH 7), 50 μM MnCl$_2$, and 50 μg/ml protein fraction. Reactions were incubated at 25° C. Specific activity of periplasmically-expressed DAHP synthase is shown in FIG. 3.

Example 3

Cell Free Production of Isobutanol and/or 1-Butanol

Current methods for production of isobutanol in *E. coli* rely on over-expression of the *E. coli* enzymes of valine biosynthesis IlvI,H,C,D in concert with overexpression of two heterologous enzymes: the alcohol dehydrogenase 2 enzyme of *S. cerevisiae* (ADH2, GenBank AAA34411.1) and the 2-keto-acid decarboxylase enzyme of *L. lactis* (KivD, GenBank CAG34226.1) (see, e.g., Atsumi et al., *Nature* (2008) 451:86). Similarly, production of 1-butanol requires the overexpression of the same two heterologous enzymes (ADH, KivD) combined with overexpression of IlvA and LeuABCD enzymes of isoleucine and leucine biosynthesis in *E. coli* (Atsumi ibid). Accumulation of higher alcohols (e.g., isobutanol, 1-butanol, n-butanol) is toxic at very low levels, 2% (w/v) (Atsumi ibid; Reyes et al., *Plos One* (2011) 6:e17678) resulting in poor cell growth and poor product titers when these pathways are active in growing *E. coli*.

Periplasmic relocation of the key enzyme diverting flux of amino acid biosynthesis precursors to isobutanol or 1-butanol would eliminate product accumulation during cell growth, and enable cell-free production post-lysis in a strain engineered to overexpress pathway enzymes as described in Atsumi et al., *Nature* (2008) 451:86. Specifically, a library of the key entry enzyme, KivD, with various periplasmic signal sequences would be created following the methods described in Examples 1 and 2. After selection of the library member exhibiting the most efficient periplasmic expression, and verification of activity, a strain engineered to produce isobutanol and 1-butanol, as described above, would be modified to include periplasmically-expressed KivD. Metabolically healthy growth of *E. coli* engineered to produce isobutanol and 1-butanol would be achieved, as the pathway would be inactive with a periplasmically-expressed KivD. Upon cell lysis, periplasmic and cytoplasmic contents would be combined activating isobutanol and 1-butanol production from glucose.

Example 4

Cell-Free Production of Isoprenoids and Terpenes

Overproduction of isoprenoids in *E. coli* requires one of two general approaches: (1) usage of the native *E. coli* deoxyxylulose-5-phosphate (DXP) pathway, or (2) usage of the non-native mevalonate (MEV)-dependent pathway (see, e.g., Martin et al., *Nat. Biotechnol.* (2003) 21:796-802). Amorphadiene, the precursor for the anti-malarial terpenoid atermisinin has been produced by the MEV pathway in *E. coli* by over-expressing the native genes atoB, idi, ispA, as well as the genes for the *S. cerevisiae* hydromethylglutaryl (HMG)-CoA synthase (ERG13, GenBank CAA90557.1), a truncated HMG-CoA reductase (HMGR, GenBank CAA86503.1), mevalonate kinase (ERG12, GenBank CAA39359.1), phosphomevalonate kinase (ERGS, GenBank CAA90191.1), mevalonate pyrophosphate decarboxylase (MVD1, GenBank CAA66158.1) and a version of the *Artemisia annua* amorphadiene synthase (ADS, GenBank AAK15697.1) codon-optimized for expression in yeast (see, e.g., Martin et al., *Nat. Biotechnol.* (2003) 21:796-802 and FIG. 5).

The prenyl diphosphate intermediates and HMG-CoA in the isoprenoid pathway described are, however, toxic and have been shown to accumulate if activity of the terpene synthase (ADS for this terpenoid) and other enzymes in the pathway are unbalanced (see, e.g., Martin et al., *Nat. Biotechnol.* (2003) 21:796-802; Withers et al., *Appl. Environ. Microbiol.* (2007) 73:6277-6283). Relocation of the key entry enzyme of this pathway, AtoB, would obviate the need to fine-tune expression in order to avoid these toxicity issues during cell growth. Specifically, a library of the key entry enzyme, AtoB, with various periplasmic signal sequences would be created following the methods described in Examples 1 and 2. After selection of the library member exhibiting the most efficient periplasmic expression, and verification of activity, an *E. coli* strain engineered to produce isoprenoids (see, e.g., Martin ibid) would be modified with periplasmically-expressed AtoB.

Metabolically healthy growth of this strain would be achieved, as the pathway would be inactive with a periplasmically-expressed AtoB. Upon cell lysis, periplasmic and cytoplasmic contents would be combined activating isoprenoid production from glucose.

Example 5

Cell Free Production of Poly-3-Hydroxybutyrate

*E. coli* has been metabolically engineered to produce poly-3-hydroxybutyrate (PHB), an important biopolymer building block, using a three-step pathway from acetyl-CoA (Tyo et al.). The three heterologous enzymes involved are the *R. eutropha* beta-ketothiolase (PhaA, GenBank CAJ92573.1) and acetoacetyl-CoA reductase (PhaB, GenBank AAA21973.1) and the *Allochromatium vinosum* PHB synthase (PhaE subunit, Gen Bank ABK60192.1; PhaC subunit, GenBank ABK60193.1).

When this pathway is active in *E. coli*, growth rate is inversely related to PHB flux due to diversion of carbon from biomass and/or the accumulation of large, toxic PHB granules in the cytoplasm (see, e.g., Tyo et al., *Metabolic Engineering* (2010) 12:187-195). Relocation of the key entry enzyme of this pathway, PhaA, would eliminate toxicity issues during cell growth. Specifically, a library of the key entry enzyme, PhaA, with various periplasmic signal sequences would be created following the methods described in Examples 1 and 2. After selection of the library member exhibiting the most efficient periplasmic expression, and verification of activity, an *E. coli* strain engineered to produce PHB (see, e.g., Tyo ibid) would be modified with periplasmically-expressed PhaA. Metabolically healthy growth of this strain would be achieved, as the pathway would be inactive with a periplasmically-expressed PhaA. Upon cell lysis, periplasmic and cytoplasmic contents would be combined activating PHB production from glucose.

Other Embodiments

As used herein, "a" or "an" means "at least one" or "one or more" unless otherwise indicated.

Unless defined otherwise, all technical and scientific terms used herein have the same meaning as is commonly understood by one of ordinary skill in the art to which this invention belongs.

All patents, patent applications (published or unpublished), literature references, books, manuals, and other publications referred to herein are incorporated by reference in their entireties. If a definition set forth herein is contrary to or otherwise inconsistent with a definition set forth in the incorporated patents, patent applications (published or unpublished), literature references, books, manuals, and/or other publications, the definition set forth herein prevails. Citation of publications or documents is not intended as an admission that any of such publications or documents are pertinent prior art, nor does it constitute any admission as to the contents or date of these publications or documents.

The foregoing has been a description of certain non-limiting embodiments of the invention. Those of ordinary skill in the art will appreciate that various changes and modifications to this description may be made without departing from the spirit or scope of the present invention, as defined in the following claims.

What is claimed is:

1. A method of producing a product of a biosynthetic pathway of interest, the method comprising:
   (a) culturing bacterial cells that express enzymes of a biosynthetic pathway for production of a product, wherein at least one of the enzymes:
      (i) is an enzyme that controls metabolic flux in the biosynthetic pathway; and
      (ii) is an enzyme modified by genetic means to attach a periplasmic-targeting sequence, thereby producing cultured bacterial cells that contain at least one of the modified enzymes sequestered into the periplasmic space, wherein the modification by genetic means and the periplasmic sequestering do not result in a deleterious increase in metabolic flux in the biosynthetic pathway;
   (b) lysing the cultured bacterial cells, thereby producing a cell lysate containing the enzymes of the biosynthetic pathway and the at least one periplasmic-targeting sequence-modified enzyme;
   (c) combining the cell lysate with one or more substance selected from the group consisting of substrates, enzymes, nutrients, co-factors, buffers, reducing agents, ATP generating systems; and
   (d) incubating the cell lysate and the one or more substance for a period of time and under conditions sufficient to enzymatically produce the product, wherein the product is selected from the group consisting of antibiotics, biosurfactants, biological fuels, amino acids, organic acids, fatty acids, alcohols, polyols, flavors, fragrances, nucleotides, vitamins, pigments, sugars, polysaccharides, biopolymers, plastics, isoprenoids, terpenes, and cell metabolites.

2. The method of claim 1, wherein the culturing bacteria cells comprises multiple cultures of said bacterial cells and/or wherein the lysing produces two or more lysates, wherein the method further comprises combining two or more of the cell lysates.

3. The method of claim 1, wherein the at least one periplasmic-targeting sequence-modified enzyme is a biosynthetic pathway entry enzyme or a rate limiting enzyme.

4. The method of claim 1, wherein the least one periplasmic-targeting sequence-modified enzyme is an enzyme that increases the rate of substrate or cofactor supplied to the biosynthetic pathway.

5. The method of claim 1, wherein in the bacterial cells a native counterpart of the at least one periplasmic-targeting sequence-modified enzyme is expressed at normal cytoplasmic levels.

6. The method of claim 1, wherein in the bacterial cells the native counterpart of the at least one periplasmic-targeting sequence-modified enzyme is knocked out.

7. The method of claim 1, wherein in the bacterial cells the at least one periplasmic-targeting sequence-modified enzyme is overexpressed.

8. The method of claim 1, wherein in the bacterial cells at least one gene encoding the at least one periplasmic-targeting sequence-modified enzyme is present on an episomal vector or a chromosome.

9. The method of claim 1, wherein in the bacterial cells at least two enzymes in the biosynthetic pathway are modified by said genetic means to attach said periplasmic targeting sequence.

10. The method of claim 1, wherein the culturing of the bacterial cells comprises culturing in cell growth medium that has been modified by the addition of a factor that increases or preserves the activity of the enzymes of the biosynthetic pathway.

11. The method of claim 1, wherein the periplasmic targeting sequence is a sequence selected from the group consisting of:

```
                                              (SEQ ID NO: 1)
MKIKTGARILALSALTTMMFSASALA;

(SEQ ID NO: 2)
MKQSTIALALLPLLFTPVTKA;

(SEQ ID NO: 3)
MMITLRKLPLAVAVAAGVMSAQAMA;

(SEQ ID NO: 4)
MNKKVLTLSAVMASMLFGAAAHA;

(SEQ ID NO: 5)
MKYLLPTAAAGLLLLAAQPAMA;

(SEQ ID NO: 6)
MKKIWLALAGLVLAFSASA;

(SEQ ID NO: 7)
MMTKIKLLMLIIFYLIISASAHA;

(SEQ ID NO: 8)
MKQALRVAFGFLILWASVLHA;

(SEQ ID NO: 9)
MRVLLFLLLSLFMLPAFS;
and (SEQ ID NO: 10)
MANNDLFQASRRRFLAQLGGLTVAGMLGPSLLTPRRATA.
```

12. The method of claim 1, wherein the product of the biosynthetic pathway is a biological fuel selected from the group consisting of bioethanol, biodiesel, and biobutanol.

13. The method of claim 1, wherein the product of the biosynthetic pathway is an alcohol or polyol, selected from the group consisting of glycerol, mannitol, erythritol, xylitol, poly-3-hydroxybutyrate, and isobutanol.

14. The method of claim 1, wherein the product of the biosynthetic pathway is a biopolymer or plastic, selected from the group consisting of polyhydroxyalkanoates, poly-γ-glutamic acid, and 1,3-propanediol.

15. The method of claim 1, wherein the product of the biosynthetic pathway is an isoprenoid or terpene, selected from the group consisting of amorphadiene, farnesene, lycopene, astaxanthin, vitamin A, menthol, and beta-carotene.

16. The method of claim 1, wherein the product of the biosynthetic pathway is a cell metabolite selected from the group consisting of 2,3-dihydroxybenzoic acid, 2-ketoglutarate, 3-phosphoglycerate, 4-hydroxybenzoate, 6-phosphogluconate, acetoacetyl-coA, acetyl-coA, acetylphosphate, adenine, adenosine, adenosine phosphosulfate, adenosine diphosphate, adenosine diphosphate-glucose, alanine, adenosine monophosphate, anthranilate, arginine, asparagine, aspartate, adenosine triphosphate, carbamylaspartate, cis-aconitate, citrate, citrulline, cytosine monophosphate, coenzyme A, cytosine triphosphate, cyclic adenosine monophosphate, cytidine, cytosine, deoxyadenosine monophosphate, deoxyadenosine triphosphate, deoxycytosine monophosphate, deoxyadenosine, deoxyguanosine, deoxyribose-5-phosphate, deoxyguanosine monophosphate, dihydroorotate, dihydroxyacetone phosphate, deoxythymidine diphosphate, deoxythymidine triphosphate, erythrose-4-phosphate, flavin adenine dinucleotide, flavin mononucleotide, fructose-1,6-bisphosphate, fructose-6-phosphate, fumarate, guanosine diphosphate, gluconate, gluconolactone, glucosamine-6-phosphate, glucose-6-phosphate, glucose-1-phosphate, glutamate, glutamine, glutathione, glutathione disulfide, glyceraldehyde-3-phosphate, glycerate, glycerol-3-phosphate, guanosine monophosphate, guanosine triphosphate, guanine, guanosine, histidine, histidinol, homocysteine, inosine diphosphate, inosine monophosphate, inosine triphosphate, isoleucine, lysine, malate, malonyl-CoA, methionine, myoinositol, N-acetyl-glucosamine-1-phosphate, N-acetylornithine, nicotinamide adenine dinucleotide, nicotinamide adenine dinucleotide hydrate, nicotinamide adenine dinucleotide phosphate, nicotinamide adenine dinucleotide phosphate hydrogen, ornithine, oxaloacetate, phenylalanine, phenylpyruvate, phosphoenolpyruvate, proline, propionyl-coA, phosphoribosyl pyrophosphate, pyruvate, quinolinate, riboflavin, ribose-5-phosphate, ribulose-5-phosphate, S-adenosyl-1-methionine, serine, shikimic acid, shikimate, succinate, succinyl-coA, threonine, tryptophan, tyrosine, uridine diphosphate, uridine diphosphate-glucose, uridine diphosphate-glucuronate, uridine diphosphate-N-acetyl-glucosamine, uridine, uridine triphosphate, valine, and xylulose-5-phosphate.

17. The method of claim 16, wherein the cell metabolite is shikimic acid or shikimate.

18. The method of claim 17, wherein the enzymes of the biosynthetic pathway are selected from the group consisting of 3-deoxy-D-arabinoheptulosonate 7-phosphate synthase, 3-dehydroquinate synthase, 3-dehydroquinate dehydratase, and shikimate dehydrogenase.

19. The method of claim 1, wherein the at least one enzyme modified by genetic means is selected from the group consisting of an oxidoreductase, a transferase, a hydrolase, a lyase, an isomerase, and a ligase.

20. A method of making a cell lysate composition for producing a product of a biosynthetic pathway of interest, the method comprising:
(a) culturing bacterial cells that express enzymes of a biosynthetic pathway for production of a product, wherein at least one of the enzymes:
  (i) is an enzyme that controls metabolic flux in the biosynthetic pathway;
  (ii) is an enzyme modified by genetic means to attach a periplasmic-targeting sequence; thereby producing cultured bacterial cells that contain at least one of the modified enzymes sequestered into the periplasmic space, wherein the modification by genetic means and the periplasmic sequestering do not result in a deleterious increase in metabolic flux in the biosynthetic pathway;
(b) lysing the cultured bacterial cells, thereby producing a cell lysate containing the enzymes of the biosynthetic pathway and the at least one periplasm-targeting sequence modified enzyme;
wherein the product is selected from the group consisting of antibiotics, biosurfactants, biological fuels, amino acids, organic acids, fatty acids, alcohols, polyols, flavors, fragrances, nucleotides, vitamins, pigments, sugars, polysaccharides, biopolymers, plastics, isoprenoids, terpenes, and cell metabolites.

21. The method of claim 20, wherein the culturing bacteria cells comprises multiple cultures of said bacterial cells and/or wherein the lysing produces two or more lysates, wherein the method further comprises combining two or more of the cell lysates.

22. The method of claim 20, wherein the at least one periplasmic-targeting sequence-modified enzyme is a biosynthetic pathway entry enzyme or a rate limiting enzyme.

23. The method of claim 20, wherein the least one periplasmic-targeting sequence-modified enzyme is an enzyme that increases the rate of substrate or cofactor supplied to the biosynthetic pathway.

24. The method of claim 20, wherein in the bacterial cells a native counterpart of the at least one periplasmic-targeting sequence-modified enzyme is expressed at normal cytoplasmic levels.

25. The method of claim 20, wherein in the bacterial cells the native counterpart of the at least one periplasmic-targeting sequence-modified enzyme is knocked out.

26. The method of claim 20, wherein in the bacterial cells the at least one periplasmic-targeting sequence-modified enzyme is overexpressed.

27. The method of claim 20, wherein in the bacterial cells at least one gene encoding the at least one periplasmic-targeting sequence-modified enzyme is present on an episomal vector or a chromosome.

28. The method of claim 20, wherein in the bacterial cells at least two enzymes in the biosynthetic pathway are modified by said genetic means to attach said periplasmic targeting sequence.

29. The method of claim 20, wherein the culturing of the bacterial cells comprises culturing in cell growth medium that has been modified by the addition of a factor that increases or preserves the activity of the enzymes of the biosynthetic pathway.

30. The method of claim 20, wherein the periplasmic targeting sequence is a sequence selected from the group consisting of:
MKIKTGARILALSALTTMMFSASALA (SEQ ID NO: 1);
MKQSTIALALLPLLFTPVTKA (SEQ ID NO: 2);

MMITLRKLPLAVAVAAGVMSAQAMA (SEQ ID NO: 3);
MNKKVLTLSAVMASMLFGAAAHA (SEQ ID NO: 4);
MKYLLPTAAAGLLLLAAQPAMA (SEQ ID NO: 5);
MKKIWLALAGLVLAFSASA (SEQ ID NO: 6);
MMTKIKLLMLIIFYLIISASAHA (SEQ ID NO: 7);
MKQALRVAFGFLILWASVLHA (SEQ ID NO: 8);
MRVLLFLLLSLFMLPAFS (SEQ ID NO: 9); and
MANNDLFQASRRRFLAQLGGLTVAGM-LGPSLLTPRRATA (SEQ ID NO: 10).

31. The method of claim 20, wherein the product of the biosynthetic pathway is a biological fuel selected from the group consisting of bioethanol, biodiesel, and biobutanol.

32. The method of claim 20, wherein the product of the biosynthetic pathway is an alcohol or polyol, selected from the group consisting of glycerol, mannitol, erythritol, xylitol, poly-3-hydroxybutyrate, and isobutanol.

33. The method of claim 20, wherein the product of the biosynthetic pathway is a biopolymer or plastic, selected from the group consisting of polyhydroxyalkanoates, poly-γ-glutamic acid, and 1,3-propanediol.

34. The method of claim 20, wherein the product of the biosynthetic pathway is an isoprenoid or terpene, selected from the group consisting of amorphadiene, farnesene, lycopene, astaxanthin, vitamin A, menthol, and beta-carotene.

35. The method of claim 20, wherein the product of the biosynthetic pathway is a cell metabolite selected from the group consisting of 2,3-dihydroxybenzoic acid, 2-ketoglutarate, 3-phosphoglycerate, 4-hydroxybenzoate, 6-phosphogluconate, acetoacetyl-coA, acetyl-coA, acetylphosphate, adenine, adenosine, adenosine phosphosulfate, adenosine diphosphate, adenosine diphosphate-glucose, alanine, adenosine monophosphate, anthranilate, arginine, asparagine, aspartate, adenosine triphosphate, carbamylaspartate, cis-aconitate, citrate, citrulline, cytosine monophosphate, coenzyme A, cytosine triphosphate, cyclic adenosine monophosphate, cytidine, cytosine, deoxyadenosine monophosphate, deoxyadenosine triphosphate, deoxycytosine monophosphate, deoxyadenosine, deoxyguanosine, deoxyribose-5-phospate, deoxyguanosine monophosphate, dihydroorotate, dihydroxyacetone phosphate, deoxythymidine diphosphate, deoxythymidine triphosphate, eyrthrose-4-phosphate, flavin adenine dinucleotide, flavin mononucleotide, fructose-1,6-bisphosphate, fructose-6-phosphate, fumarate, guanosine diphosphate, gluconate, gluconolactone, glucosamine-6-phosphate, glucose-6-phosphate, glucose-1-phosphate, glutamate, glutamine, glutathione, glutathione disulfide, glyceraldehyde-3-phosphate, glycerate, glycerol-3-phosphate, guanosine monophosphate, guanosine triphosphate, guanine, guanosine, histidine, histidinol, homocysteine, inosine diphosphate, inosine monophosphate, inosine triphosphate, isoleucine, lysine, malate, malonyl-CoA, methionine, myoinositol, N-acetyl-glucosamine-l-phosphate, N-acetylornithine, nicotinamide adenine dinucleotide, nicotinamide adenine dinucleotide hydrate, nicotinamide adenine dinucleotide phosphate, nicotinamide adenine dinucleotide phosphate hydrogen, ornithine, oxaloacetate, phenylalanine, phenylpyruvate, phosphoenolpyruvate, proline, propionyl-coA, phosphoribosyl pyrophosphate, pyruvate, quinolinate, riboflavin, ribose-5-phosphate, ribulose-5-phosphate, S-adenosyl-l-methionine, serine, shikimic acid, shikimate, succinate, succinyl-coA, threonine, tryptophan, tyrosine, uridine diphosphate, uridine diphosphate-glucose, uridine diphosphate-glucuronate, uridine diphosphate-N-acetyl-glucosamine, uridine, uridine triphosphate, valine, and xylulose-5-phosphate.

36. The method of claim 35, wherein the cell metabolite is shikimic acid or shikimate.

37. The method of claim 36, wherein the enzymes of the biosynthetic pathway are selected from the group consisting of 3-deoxy-D-arabinoheptulosonate 7-phosphate synthase, 3-dehydroquinate synthase, 3-dehydroquinate dehydratase, and shikimate dehydrogenase.

38. The method of claim 20, wherein the at least one enzyme modified by genetic means is selected from the group consisting of an oxidoreductase, a transferase, a hydrolase, a lyase, an isomerase, and a ligase.

* * * * *

UNITED STATES PATENT AND TRADEMARK OFFICE
CERTIFICATE OF CORRECTION

PATENT NO. : 8,956,833 B2
APPLICATION NO. : 13/102967
DATED : February 17, 2015
INVENTOR(S) : James R. Swartz It is certified that error appears in the above-identified patent and that said Letters Patent is hereby corrected as shown below:

*In the Specification*

At column 15, lines 52-59, please change the sentence:

"However, other known bacterial or bacteriophage promoters are also suitable, *e.g.* the lacd promoter, the lacZ promoter, the T3 promoter, the T7 promoter, the arabinose promoter ,the gpt promoter, the lambda PR promoter, the lambda PL promoter, promoters from operons encoding glycolytic enzymes such as 3-phosphoglycerate kinase (PGK), and the acid phosphatase promoter."

to

--However, other known bacterial or bacteriophage promoters are also suitable, *e.g.* the lacI promoter, the lacZ promoter, the T3 promoter, the T7 promoter, the arabinose promoter, the gpt promoter, the lambda PR promoter, the lambda PL promoter, promoters from operons encoding glycolytic enzymes such as 3-phosphoglycerate kinase (PGK), and the acid phosphatase promoter.--.

At column 31, in Table 5, please change the language "Reverse primer for additionof C-term 6×His tag to all constructs" to --Reverse primer for addition of C-term 6×His tag to all constructs--.

At column 33, line 64, please change the language "phosphomevalonate kinase (ERGS, GenBank CAA90191.1)," to --phosphomevalonate kinase (ERG8, GenBank CAA90191.1),--.

Signed and Sealed this
Twenty-third Day of June, 2015

Michelle K. Lee
*Director of the United States Patent and Trademark Office*

SEQUENCE LISTING

```
<160> NUMBER OF SEQ ID NOS: 25

<210> SEQ ID NO 1
<211> LENGTH: 26
<212> TYPE: PRT
<213> ORGANISM: E. coli

<400> SEQUENCE: 1

Met Lys Ile Lys Thr Gly Ala Arg Ile Leu Ala Leu Ser Ala Leu Thr
1               5                   10                  15

Thr Met Met Phe Ser Ala Ser Ala Leu Ala
            20                  25

<210> SEQ ID NO 2
<211> LENGTH: 21
<212> TYPE: PRT
<213> ORGANISM: E. coli

<400> SEQUENCE: 2

Met Lys Gln Ser Thr Ile Ala Leu Ala Leu Leu Pro Leu Leu Phe Thr
1               5                   10                  15

Pro Val Thr Lys Ala
            20

<210> SEQ ID NO 3
<211> LENGTH: 25
<212> TYPE: PRT
<213> ORGANISM: E. coli

<400> SEQUENCE: 3

Met Met Ile Thr Leu Arg Lys Leu Pro Leu Ala Val Ala Val Ala Ala
1               5                   10                  15

Gly Val Met Ser Ala Gln Ala Met Ala
            20                  25

<210> SEQ ID NO 4
<211> LENGTH: 23
<212> TYPE: PRT
<213> ORGANISM: E. coli

<400> SEQUENCE: 4

Met Asn Lys Lys Val Leu Thr Leu Ser Ala Val Met Ala Ser Met Leu
1               5                   10                  15

Phe Gly Ala Ala Ala His Ala
            20

<210> SEQ ID NO 5
<211> LENGTH: 22
<212> TYPE: PRT
<213> ORGANISM: E. caratorova

<400> SEQUENCE: 5

Met Lys Tyr Leu Leu Pro Thr Ala Ala Ala Gly Leu Leu Leu Leu Ala
1               5                   10                  15
```

Ala Gln Pro Ala Met Ala
            20

<210> SEQ ID NO 6
<211> LENGTH: 19
<212> TYPE: PRT
<213> ORGANISM: E. coli

<400> SEQUENCE: 6

Met Lys Lys Ile Trp Leu Ala Leu Ala Gly Leu Val Leu Ala Phe Ser
1               5                   10                  15

Ala Ser Ala

<210> SEQ ID NO 7
<211> LENGTH: 23
<212> TYPE: PRT
<213> ORGANISM: E. coli

<400> SEQUENCE: 7

Met Met Thr Lys Ile Lys Leu Leu Met Leu Ile Ile Phe Tyr Leu Ile
1               5                   10                  15

Ile Ser Ala Ser Ala His Ala
            20

<210> SEQ ID NO 8
<211> LENGTH: 21
<212> TYPE: PRT
<213> ORGANISM: E. coli

<400> SEQUENCE: 8

Met Lys Gln Ala Leu Arg Val Ala Phe Gly Phe Leu Ile Leu Trp Ala
1               5                   10                  15

Ser Val Leu His Ala
            20

<210> SEQ ID NO 9
<211> LENGTH: 18
<212> TYPE: PRT
<213> ORGANISM: E. coli

<400> SEQUENCE: 9

Met Arg Val Leu Leu Phe Leu Leu Leu Ser Leu Phe Met Leu Pro Ala
1               5                   10                  15

Phe Ser

<210> SEQ ID NO 10
<211> LENGTH: 39
<212> TYPE: PRT
<213> ORGANISM: E. coli

<400> SEQUENCE: 10

Met Ala Asn Asn Asp Leu Phe Gln Ala Ser Arg Arg Arg Phe Leu Ala
1               5                   10                  15

Gln Leu Gly Gly Leu Thr Val Ala Gly Met Leu Gly Pro Ser Leu Leu
            20                  25                  30

Thr Pro Arg Arg Ala Thr Ala
        35

<210> SEQ ID NO 11
<211> LENGTH: 45
<212> TYPE: DNA

```
<213> ORGANISM: Artificial sequence
<220> FEATURE:
<223> OTHER INFORMATION: Synthetic aroG PCR primer

<400> SEQUENCE: 11
gcaattcggt ctcccatgaa ttatcagaac gacgatttac gcatc          45

<210> SEQ ID NO 12
<211> LENGTH: 35
<212> TYPE: DNA
<213> ORGANISM: Artificial sequence
<220> FEATURE:
<223> OTHER INFORMATION: Synthetic aroG PCR primer

<400> SEQUENCE: 12
gaattcgcgg ccgcttaccc gcgacgcgct tttac                     35

<210> SEQ ID NO 13
<211> LENGTH: 42
<212> TYPE: DNA
<213> ORGANISM: Artificial sequence
<220> FEATURE:
<223> OTHER INFORMATION: Synthetic aroG PCR primer

<400> SEQUENCE: 13
gcaattcggt ctcccatgaa aaaaacggca attgcgatag cg              42

<210> SEQ ID NO 14
<211> LENGTH: 35
<212> TYPE: DNA
<213> ORGANISM: Artificial sequence
<220> FEATURE:
<223> OTHER INFORMATION: Synthetic aroG PCR primer

<400> SEQUENCE: 14
gaattcgcgg ccgcttaccc gcgacgcgct tttac                     35

<210> SEQ ID NO 15
<211> LENGTH: 43
<212> TYPE: DNA
<213> ORGANISM: Artificial sequence
<220> FEATURE:
<223> OTHER INFORMATION: Synthetic aroG PCR primer

<400> SEQUENCE: 15
gcaattcggt ctcccatgaa aaaaaatatt gctttcctgc tcg             43

<210> SEQ ID NO 16
<211> LENGTH: 35
<212> TYPE: DNA
<213> ORGANISM: Artificial sequence
<220> FEATURE:
<223> OTHER INFORMATION: Synthetic aroG PCR primer

<400> SEQUENCE: 16
gaattcgcgg ccgcttaccc gcgacgcgct tttac                     35

<210> SEQ ID NO 17
<211> LENGTH: 39
<212> TYPE: DNA
<213> ORGANISM: Artificial sequence
<220> FEATURE:
<223> OTHER INFORMATION: Synthetic aroG PCR primer

<400> SEQUENCE: 17
gcaattcggt ctcccatgaa aaagatttgg ctggcgctg                  39
```

<210> SEQ ID NO 18
<211> LENGTH: 35
<212> TYPE: DNA
<213> ORGANISM: Artificial sequence
<220> FEATURE:
<223> OTHER INFORMATION: Synthetic aroG PCR primer

<400> SEQUENCE: 18
gaattcgcgg ccgcttaccc gcgacgcgct tttac        35

<210> SEQ ID NO 19
<211> LENGTH: 43
<212> TYPE: DNA
<213> ORGANISM: Artificial sequence
<220> FEATURE:
<223> OTHER INFORMATION: Synthetic aroG PCR primer

<400> SEQUENCE: 19
gcaattcggt ctcccatgaa aataaaaaca ggtgcacgca tcc        43

<210> SEQ ID NO 20
<211> LENGTH: 35
<212> TYPE: DNA
<213> ORGANISM: Artificial sequence
<220> FEATURE:
<223> OTHER INFORMATION: Synthetic aroG PCR primer

<400> SEQUENCE: 20
gaattcgcgg ccgcttaccc gcgacgcgct tttac        35

<210> SEQ ID NO 21
<211> LENGTH: 41
<212> TYPE: DNA
<213> ORGANISM: Artificial sequence
<220> FEATURE:
<223> OTHER INFORMATION: Synthetic aroG PCR primer

<400> SEQUENCE: 21
gcaattcggt ctcccatgaa acaaagcact attgcactgg c        41

<210> SEQ ID NO 22
<211> LENGTH: 35
<212> TYPE: DNA
<213> ORGANISM: Artificial sequence
<220> FEATURE:
<223> OTHER INFORMATION: Synthetic aroG PCR primer

<400> SEQUENCE: 22
gaattcgcgg ccgcttaccc gcgacgcgct tttac        35

<210> SEQ ID NO 23
<211> LENGTH: 45
<212> TYPE: DNA
<213> ORGANISM: Artificial sequence
<220> FEATURE:
<223> OTHER INFORMATION: Synthetic aroG PCR primer

<400> SEQUENCE: 23
gcaattcggt ctcccatgat gactaaaata aagttattga tgctc        45

<210> SEQ ID NO 24
<211> LENGTH: 35
<212> TYPE: DNA
<213> ORGANISM: Artificial sequence
<220> FEATURE:

```
<223> OTHER INFORMATION: Synthetic aroG PCR primer

<400> SEQUENCE: 24
gaattcgcgg ccgcttaccc gcgacgcgct tttac                        35

<210> SEQ ID NO 25
<211> LENGTH: 51
<212> TYPE: DNA
<213> ORGANISM: Artificial sequence
<220> FEATURE:
<223> OTHER INFORMATION: Synthetic aroG PCR primer

<400> SEQUENCE: 25
gaatgcggcc gcttagtggt gatgatggtg atgcccgcga cgcgcttta c       51
```